United States Patent
Kay et al.

(10) Patent No.: US 9,381,226 B2
(45) Date of Patent: Jul. 5, 2016

(54) METHODS AND COMPOSITIONS RELATED TO INHIBITION OF VIRAL ENTRY

(75) Inventors: Michael S. Kay, Salt Lake City, UT (US); Brett D. Welch, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 1173 days.

(21) Appl. No.: 12/526,071

(22) PCT Filed: Feb. 8, 2008

(86) PCT No.: PCT/US2008/053447
§ 371 (c)(1),
(2), (4) Date: Feb. 4, 2010

(87) PCT Pub. No.: WO2008/098182
PCT Pub. Date: Aug. 14, 2008

(65) Prior Publication Data
US 2010/0184663 A1    Jul. 22, 2010

Related U.S. Application Data

(60) Provisional application No. 60/888,944, filed on Feb. 8, 2007.

(51) Int. Cl.
*A61K 38/02* (2006.01)
*A61K 38/10* (2006.01)
*A61K 47/48* (2006.01)
*C07K 5/117* (2006.01)
*C07K 7/06* (2006.01)
*G01N 33/50* (2006.01)
*G01N 33/569* (2006.01)

(52) U.S. Cl.
CPC .............. *A61K 38/10* (2013.01); *A61K 47/481* (2013.01); *A61K 47/48215* (2013.01); *A61K 47/48253* (2013.01); *C07K 5/1024* (2013.01); *C07K 7/06* (2013.01); *G01N 33/5008* (2013.01); *G01N 33/56983* (2013.01); *G01N 2333/005* (2013.01); *G01N 2333/162* (2013.01); *G01N 2500/00* (2013.01)

(58) Field of Classification Search
None
See application file for complete search history.

(56) References Cited

U.S. PATENT DOCUMENTS

| 6,506,554 | B1 | 1/2003 | Chan et al. | |
| 6,818,740 | B1 * | 11/2004 | Eckert et al. | 530/327 |
| 6,841,657 | B2 * | 1/2005 | Eckert et al. | 530/324 |

FOREIGN PATENT DOCUMENTS

| WO | 2005/018666 A1 | 3/2005 |
| WO | WO 2005/080418 A2 | 9/2005 |

OTHER PUBLICATIONS

Miller et al. PNAS 2005, vol. 102, pp. 14759-14764.*
International Search Report mailed May 8, 2008 in related International Patent Application No. PCT/US08/53447.
Written Opinion of the International Searching Authority issued Aug. 5, 2009 in International Patent Application No. PCT/US08/53447.
Eckert et al., "Inhibiting HIV-1 Entry: Discovery of D-Peptide Inhibitors that Target the gp41 Coiled-Coil Pocket," *Cell*. 99:103-115, Oct. 1, 1999.

* cited by examiner

*Primary Examiner* — Shanon A Foley
*Assistant Examiner* — Myron Hill
(74) *Attorney, Agent, or Firm* — Seed IP Law Group PLLC

(57) ABSTRACT

Disclosed are compositions and methods for inhibiting viral entry.

13 Claims, 7 Drawing Sheets

METHODS AND COMPOSITIONS RELATED TO INHIBITION OF VIRAL ENTRY

CROSS-RELATED APPLICATIONS

This application claims the benefit of U.S. provisional application No. 60/888,944, filed Feb. 8, 2007. The aforementioned application is herein incorporated by this reference in its entirety.

ACKNOWLEDGEMENTS

This work was supported in part by the National Institute of Health Grant Numbers GM P01 066521 and AI 076168. The United States Government has certain rights in the invention.

BACKGROUND

HIV entry is mediated by the viral envelope glycoprotein, which comprises non-covalently associated surface (gp120) and transmembrane (gp41) subunits. gp120 is primarily involved in recognition of cellular receptors, while gp41 directly mediates membrane fusion. When peptides isolated from the gp41 N- and C-peptide regions (N- and C-peptides) are mixed in solution, they form a six-helix bundle, which represents the post-fusion gp41 structure (Lu 1995; Chan 1997; Weissenhorn 1997; Tan 1997). Three N-peptides form a central parallel trimeric coiled coil (N-trimer) surrounded by three antiparallel helical C-peptides that nestle into long grooves between neighboring N-peptides. The importance of this structure is indicated by the dominant negative inhibition of HIV entry by N- and C-peptides (Wild 1992; Jiang 1993; Eckert 2001).

The available inhibitory and structural data support a working model of HIV membrane fusion (FIG. 1) (Weissenhorn 1997; Eckert 2001; Chan 1998). Initially, gp120 interacts with cellular CD4 and a chemokine coreceptor (typically CXCR4 or CCR5), causing large conformational changes in gp120 that propagate to gp41 via the gp41-gp120 interface. gp41 then undergoes a massive structural rearrangement that unleashes its N-terminal fusion peptide, which embeds in the target cell membrane. At this stage of fusion, gp41 adopts an extended "prehairpin intermediate" conformation that bridges both viral and cellular membranes and exposes the N-trimer region. This intermediate is relatively long-lived (minutes) (Eckert 2001; Chan 1998; Furuta 1998), but ultimately collapses as the N- and C-peptide regions of each gp41 monomer associate to form a hairpin structure. Three such hairpins (trimer-of-hairpins) form the 6-helix bundle, which forces the viral and cellular membranes into tight apposition and leads to membrane fusion.

According to this model, an inhibitor that binds to the N-trimer and prevents hairpin formation can inhibit viral entry. This has been well supported by the discovery of numerous peptide, protein, and small molecule inhibitors that bind the N-trimer (Root 2004). A particularly interesting feature of the N-trimer is the deep hydrophobic "pocket" formed by its 17 C-terminal residues. This pocket has several enticing features as an inhibitory target including: (1) a very highly conserved sequence (Chan 1997; Eckert 1999; Root 2001), (2) an essential role in viral entry (Chan 1998), (3) a compact binding site vulnerable to inhibition by small molecules or short peptides, and (4) the availability of several designed peptides (e.g., IQN17 (Eckert 1999), IZN17 (Eckert 2001), 5-helix (Root 2001), $N_{CCG}N13$ (Louis 2003) that authentically mimic the pocket structure.

Fuzeon is an approved HIV-1 entry inhibitor (also known as T-20 or enfuvirtide, Trimeris), which is a 36-residue C-peptide that binds to the N-trimer groove, but not the pocket (Wild 1994; Rimsky 1998). Although a significant breakthrough, Fuzeon has several serious limitations that have hampered its widespread clinical adoption, including high dosing requirements (90 mg, twice daily via injection), high cost (>$25,000 per patient per year), and the emergence of resistant strains both in vitro (Rimsky 1998) and in patients (Wei 2002). These problems have limited Fuzeon's clinical use to patients with multidrug resistant HIV-1 (salvage therapy).

Many of Fuzeon's limitations stem from protease sensitivity, a common problem for all L-peptide drugs. In contrast, D-peptide drugs have several theoretical advantages, including: (1) D-peptides are resistant to proteases (Milton 1992), a property that can dramatically increase serum half-life (Sadowski 2004), (2) L-peptides must be injected to avoid digestion, but short D-peptides can be absorbed systemically when taken orally (Pappenheimer 1994; Pappenheimer 1997), and (3) D-peptides represent a rich source of structural diversity because they can bind to targets with unique interface geometries not available to L-peptides. Despite these advantages, however, the potential of D-peptides has been largely unfulfilled.

Eckert et al. used mirror-image phage display (Schumacher 1996) to discover D-peptides that bind to the N-trimer pocket and inhibit HIV-1 entry with modest potency (Eckert 1999). These D-peptides provided the first direct proof that binding to the hydrophobic pocket is sufficient to block HIV-1 entry. Numerous other attempts to develop potent, pocket-specific entry inhibitors, include: minimized C-peptides (Judice 1997; Jin 2000; Sia 2002), helical mimics (Ernst 2002; Stephens 2005), and small molecules (Debnath 1999; Ferrer 1999; Zhao 2002; Jiang 2004; Frey 2006). However, at present, all of these inhibitors suffer from limited potency and/or toxicity in standard viral infectivity or cell-cell fusion assays.

What is needed in the art are peptides that can potently inhibit the entry of gp41 into cells.

SUMMARY

Disclosed herein is an isolated composition comprising two or more linked peptides, wherein at least one peptide interacts with the N-trimer pocket of a viral transmembrane protein (TM).

Also disclosed is a method for inhibition of transmission of a virus to a cell, comprising exposing the virus to an isolated composition comprising two or more linked peptides, wherein at least one peptide interacts with the N-trimer pocket of a viral transmembrane protein (TM), thereby inhibiting transmission of the virus to the cell.

Further disclosed is a method for inhibiting viral entry into a cell, comprising exposing the virus to an isolated composition comprising two or more linked peptides, wherein at least one peptide interacts with the N-trimer pocket of a viral transmembrane protein (TM), thereby inhibiting viral entry into a cell.

Disclosed herein is a method of treating a viral infection in a subject comprising administering to the subject an effective amount of an isolated composition comprising two or more linked peptides, wherein at least one peptide interacts with the N-trimer pocket of a viral transmembrane protein (TM), wherein the composition is in a pharmaceutical carrier.

Further disclosed is an isolated peptide which interacts with the N-trimer pocket of a viral transmembrane protein, wherein the peptide is less than 10 amino acid residues in length.

Also disclosed is a method for inhibition of transmission of a virus to a cell, comprising exposing the virus to an isolated peptide which interacts with the N-trimer pocket of a viral transmembrane protein, wherein the peptide is less than 10 amino acid residues in length, thereby inhibiting transmission of the virus to the cell.

Also disclosed herein is a method for inhibiting viral entry, comprising exposing the virus to an isolated peptide which interacts with the N-trimer pocket of a viral transmembrane protein, wherein the peptide is less than 10 amino acid residues in length, thereby inhibiting viral entry into a cell.

Further disclosed is a method of treating a viral infection in a subject comprising administering to the subject an effective amount of an isolated peptide which interacts with the N-trimer pocket of a viral transmembrane protein, wherein the peptide is less than 10 amino acid residues in length, wherein the composition is in a pharmaceutical carrier.

Disclosed herein is a method for evaluating the ability of a composition comprising a peptide of less than 10 core residues in length to interact with the N-trimer pocket of a viral transmembrane protein (TM), thereby inhibiting viral entry into a cell, comprising: a. incubating the composition and a cell under conditions sufficient to allow the components to interact; b. contacting the components of step a) with a virus; and c. evaluating the ability of the composition to inhibit viral entry into the cell.

Further disclosed is a composition comprising two or more linked peptides and an N-trimer molecule, wherein the two or more linked peptides, when associated with the N-trimer molecule, has an increased affinity for the N-trimer molecule, when compared with the affinity of a single peptide for the N-trimer molecule.

Also disclosed is a composition comprising two or more linked peptides and an N-trimer molecule, wherein the two or more linked peptides, when associated with the N-trimer molecule, has enhanced antiviral activity when compared with the antiviral activity of a single peptide.

Disclosed herein is a method of evaluating the ability of a composition comprising two or more linked peptides with increased affinity for an N-trimer molecule when compared with the affinity of one of a single peptide, comprising: a. incubating a test composition and an N-trimer molecule; b. measuring the affinity of the test composition for the N-trimer molecule; c. comparing the affinity of the test composition for the N-trimer molecule with the affinity for the N-trimer molecule of a single peptide.

Also disclosed is a method of identifying a composition comprising two or more linked peptides with enhanced antiviral activity for an N-trimer molecule when compared with the antiviral activity of a single peptide, comprising: a. incubating a test composition with a cell; b. contacting the components of step (a) with a virus; c. measuring the antiviral activity of the test composition; and d. comparing the antiviral activity of the test composition with the antiviral activity of a single peptide.

Also disclosed is a method for identifying peptides that interact with an N-trimer of a transmembrane protein, comprising: a. exposing one or more test peptides and a competitor to an N-trimer of a transmembrane protein, wherein the competitor can interact with the N-trimer; b. identifying which test peptides successfully interact with the N-trimer in the presence of the competitor; c. increasing concentration of the competitor one or more times and repeating steps a)-b), wherein those test peptides that continue to interact with the N-trimer in the presence of increased concentration of competitor are identified, thereby identifying peptides that interact with an N-trimer of a transmembrane protein.

Disclosed is a method for identifying peptides that interact with an N-trimer of a transmembrane protein, comprising: exposing one or more test peptides and a competitor to an N-trimer of a transmembrane protein, wherein the competitor can interact with the N-trimer; identifying which test peptides successfully interact with the N-trimer in the presence of the competitor; c. exposing the test peptides identified in step b) to a different competitor with an increased affinity for the N-trimer as compared to the first competitor; d. repeating step c) one or more times, wherein those test peptides that continue to interact with the N-trimer in the presence of a competitor are identified, thereby identifying peptides that interact with an N-trimer of a transmembrane protein.

BRIEF DESCRIPTION OF THE DRAWINGS

The accompanying drawings, which are incorporated in and constitute a part of this specification, illustrate several embodiments and together with the description illustrate the disclosed compositions and methods.

DETAILED DESCRIPTION

Figure 1:
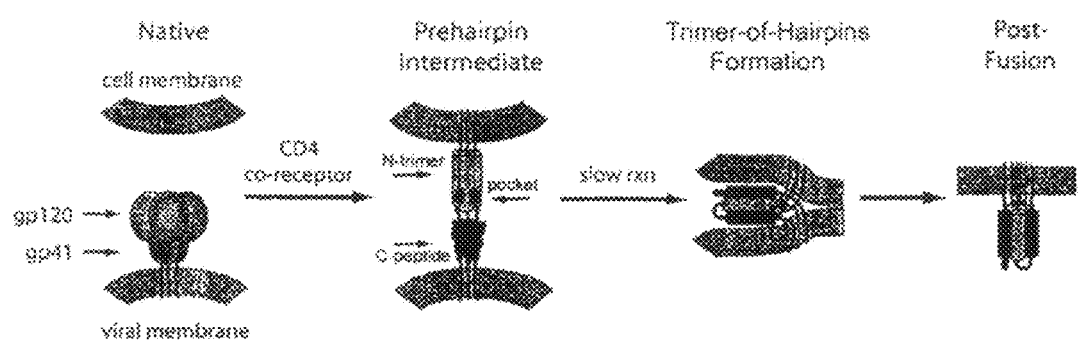
FIG. 1 shows an HIV entry pathway. Upon cellular receptor recognition, gp120 and gp41 undergo conformational changes resulting in the exposure of the N-trimer in the prehairpin intermediate. Formation of the trimer-of-hairpins structure juxtaposes cellular and viral membranes and causes fusion. The gp41 fusion peptide (red), and transmembrane domain (purple) are also shown. For clarity, gp120 is omitted from the prehairpin intermediate. Adapted from Ref. (Hamburger 2005).

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. INHIBITING VIRAL ENTRY

The gp41 subunit of the HIV-1 envelope protein mediates fusion of viral and cellular membranes. The crystal structure of the gp41 ectodomain core is a six-helix bundle composed of three helical hairpins, each consisting of an N-helix paired with an antiparallel C-helix (D. C. Chan, D. Fass, J. M. Berger, P. S. Kim, Cell, 89:263 (1997), W. Weissenhorn, A. Dessen, S. C. Harrison, J. J. Skehel, D. C. Wiley, Nature, 387:426 (1997); K. Tan, J. Liu, J. Wang, S. Shen, M. Lu, Proc. Natl. Acad. Sci. USA, 94:12303 (1997). Three N-helices form an interior, trimeric coiled-coil, and three C-helices wrap around the outside of this N-helix coiled-coil along conserved, hydrophobic grooves. This structure likely corresponds to the core of the fusion-active state of gp41 (discussed in D. C. Chan, D. Fass, J. M. Berger, P. S. Kim, Cell, 89:263 (1997), and D. C. Chan and Peter S. Kim, Cell, 93:681 (1998)) and shows similarity to the proposed fusogenic structures of envelope fusion proteins from influenza (P. A. Bullough, F. M. Hughson, J. J. Skehel, D. C. Wiley, Nature, 371:37 (1994)), Moloney Murine Leukemia Virus (D. Fass, S. C. Harrison, P. S. Kim, Nat. Struct. Biol., 3:465 (1996)), and simian immunodeficiency virus (SIV). (V. N. Malashkevich, D. C. Chan, C. T. Chutkowski, P. S. Kim, Proc. Natl. Acad. Sci. USA, 95:9134 (1998), M. Caffrey et al., EMBO J., 17:4572 (1998)), and Ebola virus (W. Weissenhorn et al., Mol. Cell 2:605 (1998), V. N. Malashkevich et al., Proc. Natl. Acad. Sci. USA, 96:2662 (1999).)

Synthetic C-peptides (peptides corresponding to the C-helix), such as DP178 and C34, are potent inhibitors of HIV-1 membrane fusion and are effective against both laboratory-adapted strains and primary isolates (V. N. Malashkevich, D. C. Chan, C. T. Chutkowski, P. S. Kim, Proc. Natl. Acad. Sci. USA, 95:9134 (1998), DP178 corresponds to residues 638-673 of HIV-1 gp41 and is acetylated at the amino terminus and amidated at the carboxy terminus (C. T. Wild, D. C. Shugars, T. K. Greenwell, C. B. McDanal, T. J. Matthews, Proc. Natl. Acad. Sci. USA, 91:9770 (1994), S. Jiang, K. Lin, N. Strick, A. R. Neurath, Nature, 365:113 (1993)). A Phase I clinical trial with the C-peptide DP 178 (also called T-20) indicates that it has antiviral activity in vivo, resulting in reduced viral loads (M. Saag, et al., abstract #771 presented at the Infectious Disease Society of America 35th Annual Meeting, San Francisco, Calif., 16 Sep. 1997; Kilby, J. M. et al. Nature Med. 4:1302-1307 (1998)). Based on the structural features of the gp41 core, these peptides are thought to act through a dominant-negative mechanism, in which exogenous C-peptides bind to the central coiled-coil of gp41 and lead to its inactivation (D. C. Chan and P. S. Kim, Cell, 93:681 (1998); R. A. Furuta et al., Nat. Struct. Biol., 5:276 (1998); D. C. Chan, D. Fass, J. M. Berger, P. S. Kim, Cell, 89:263 (1997), W. Weissenhorn, A. Dessen, S. C. Harrison, J. J. Skehel, D. C. Wiley, Nature, 387:426 (1997); K. Tan, J. Liu, J. Wang, S. Shen, M. Lu, Proc. Natl. Acad. Sci. USA, 94:12303 (1997), M. Lu, S. C. Blacklow, P. S. Kim, Nat. Struct. Biol., 2:1075 (1995) and C. H. Chen, T. J. Matthews, C. B. McDanal, D. P. Bolognesi, M. L. Greenberg, J. Virol., 69:3771 (1995)). These peptides likely act on a pre-hairpin intermediate of gp41 that forms when the native gp41 structure (i.e., the nonfusogenic conformation present on free virions) is perturbed by gp120/CD4/coreceptor interactions. This pre-hairpin intermediate is proposed to have an exposed N-coiled-coil, thereby allowing C-peptides to bind and inactivate gp41 prior to the formation of the fusion-active hairpin structure (D. C. Chan, P. S. Kim, Cell, 93:681 (1998)). This model is further supported by immunoprecipitation experiments indicating that the C-peptide DP178 binds to gp41 (R. A. Furuta, C. T. Wild, Y. Weng, C. D. Weiss, Nat. Struct. Biol., 5:276 (1998)). In addition, viruses escaping DP178 inhibition show mutations in the central coiled-coil region of gp41 (L. T. Rimsky, D. C. Shugars, T. J. Matthews, J. Virol., 72:986 (1998)).

Crystallographic studies of gp41 have facilitated the development of small-molecule peptidomimetic drugs which, in contrast to C-peptides, have the potential to be orally administered. Within each coiled-coil interface is a deep cavity, formed by a cluster of residues in the N-helix coiled-coil, that is an attractive target for the development of antiviral compounds. Three residues from the C-helix (Trp$^{628}$, Trp$^{631}$, and Ile$^{635}$) insert into this cavity and make extensive hydrophobic contacts. Mutational analysis indicates that two of the N-helix residues (Leu$^{568}$ and Trp$^{571}$) comprising this cavity are critical for membrane fusion activity (J. Cao, et al., J. virol., 67:2747 (1993)). Therefore, compounds that bind with high affinity to this cavity and prevent normal N- and C-helix pairing are effective HIV-1 inhibitors. In addition, residues in the cavity are highly conserved among diverse HIV-1 isolates. Because of the high structural conservation, drugs targeting this site would have broad activity against diverse HIV isolates.

Small-molecule inhibitors directed against the cavity of the central coiled-coil target one of the most highly conserved regions of the HIV-1 envelope proteins. The analogous cavity in the SIV gp41 core has an essentially identical structure, with conservation of side chain conformations (V. N. Malashkevich, D. C. Chan, C. T. Chutkowski, P. S. Kim, Proc. Natl. Acad. Sci. USA, 95:9134 (1998)). This high degree of structural conservation explains the broad neutralizing activity of C-peptides, which are effective against laboratory-adapted strains as well as primary isolates (C. T. Wild, D. C. Shugars, T. K. Greenwell, C. B. McDanal, T. J. Matthews, Proc. Natl. Acad. Sci. USA, 91:9770 (1994), S. Jiang, K. Lin, N. Strick, A. R. Neurath, Nature, 365:113 (1993)). Remarkably, SIV C34 peptide is nearly as effective as HIV-1 C34 in inhibiting HIV-1 infection (V. N. Malashkevich, D. C. Chan, C. T. Chutkowski, P. S. Kim, Proc. Natl. Acad. Sci. USA, 95:9134 (1998)). In addition, a C-peptide (T649) containing the cavity-binding region is much less susceptible to the evolution of resistant virus (L. T. Rimsky, D. C. Shugars, T. J. Matthews, J. Virol., 72:986 (1998)) than DP178 (also called T-20), which lacks this region. These observations are evidence that high-affinity ligands targeting the coiled-coil surface, particularly its cavity, can have broad activity against diverse HIV isolates (including HIV-2) and are less likely to be bypassed by drug-escape mutants.

As described herein, the pocket on the surface of the N-helix coiled-coil of HIV-1 envelope protein gp41 subunit is a drug target. Similarly, cavities on other pathogens (e.g., HIV-2) which can cause AIDS or on pathogens which cause AIDS-like conditions in nonhuman mammals (e.g., SIV) are also drug targets. As described herein, available methods (e.g., mirror image phage display methods, combinational chemistry, computational approaches and other drug screening and medicinal chemistry methods) can be used to identify peptides, D-peptides, including multimers, and peptidomimetics and small molecules that bind the coiled-coil cavity of HIV-1 (and/or HIV-2) with sufficient affinity to interfere with viral entry into cells and, thus, inhibit viral infection. Mirror image phage display has been used to identify D-peptides which bind to a cavity on the surface of the N-helix coiled-coil of HIV-1 gp41.

C. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed in a multimer, and a number of modifications that can be made to a number of molecules including the peptide are discussed, specifically contemplated is each and every combination and permutation of the peptide in the multimer with other peptides in the multimer, as well as the modifications to the peptides that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Peptides

Disclosed herein are peptides and multimers of those peptides. For example, disclosed is a peptide which interacts with the N-trimer pocket of a viral transmembrane protein. For example, the peptides can bind to a cavity on the surface of the N-helix coiled-coil of HIV envelope glycoprotein gp41 (e.g., HIV-1, HIV-2). Such peptides can be of any length, provided that they are of sufficient length to bind the cavity in such a manner that they interfere with the interaction of the N-helix coiled-coil cavity and amino acid residues of the C-peptide region of viral gp41 and prevent, or inhibit, viral entry into the cells. For example, the peptide can comprise at least 2, 3, 4, 5, 6, 7, 8, 9, or 10 core amino acid residues in length. The amino acid residues can be naturally occurring or non-naturally occurring or modified, as described below. The peptides can be linear or circular.

By "inhibit viral transmembrane protein" is meant a reduction in the number of viral particles that are capable of entering a cell. It can mean complete inhibition, in other words no viral particles are capable of entering a cell, or it can mean a partial inhibition, meaning that in a given system there is a reduction in the number of viral particles capable of entering a cell when compared with a non-treated system, or a control. There can be a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% reduction in the number of viral particles that are capable of entering a cell, or any amount greater, less, or in between these amounts.

Examples of D-peptides, identified as described herein, are shown below. Because of library design, each peptide, in addition to the amino acid residues shown, is flanked by GA on the N-terminus and AA on the C-terminus. N-terminal lysine residues were added to improve water solubility. Some of the peptides are also shown with the linker sequence "PEG" before the amino acid sequence.

Disclosed in Table 1 are various D-peptides that can be used with the methods and compositions disclosed herein:

TABLE 1

D-peptide binding and neutralization

| Sample | Sequence | |
|---|---|---|
| D10-p5 | KKGACELLGWEWAWLCAA | (SEQ ID NO: 1) |
| 2K-PIE1 | KKGACESPEWRWLCAA | (SEQ ID NO: 2) |
| 2K-PIE2 | KKGACDYPEWRWLCAA | (SEQ ID NO: 3) |
| PIE2-AAA | KGACDYPEWRWLCAAA | (SEQ ID NO: 4) |
| PIE2 | KGACDYPEWRWLCAA | (SEQ ID NO: 5) |
| PIE7 | KGACDYPEWQWLCAA | (SEQ ID NO: 6) |
| PIE8 | KGACDYKEWQWLCAA | (SEQ ID NO: 7) |
| PEG-PIE7 | PEG-KGACDYPEWQWLCAA | (SEQ ID NO: 8) |
| PEG-(PIE7)$_2$ | PEG-(KGACDYPEWQWLCAA)$_2$ | (SEQ ID NO: 9) |
| 2K-PhD1 | KKGACPREWHWLCAA | (SEQ ID NO: 10) |
| PhD1 | GACPREWHWLCAA | (SEQ ID NO: 11) |
| 2K-PIE0 | KKGAGDYWEWRWLCAA | (SEQ ID NO: 12) |
| D-PIE2 | DGACDYPEWRWLCAA | (SEQ ID NO: 13) |
| 2K-PIE3 | KKGACDDPDWQWLCAA | (SEQ ID NO: 14) |
| 2K-PIE4 | KKGACEDPDWQWLCAA | (SEQ ID NO: 15) |
| 2K-PIE5 | KKGACEDPEWQWLCAA | (SEQ ID NO: 16) |
| 2K-PIE6 | KKGACNDPEWQWLCAA | (SEQ ID NO: 17) |
| PIE1 | DGACESPEWQWLCAAGAA | (SEQ ID NO: 18) |
| R4#9 | ACPPEWHWLCGGGSA | (SEQ ID NO: 19) |
| R4#12 | ACPVEWRWLCGGGSA | (SEQ ID NO: 20) |

TABLE 1-continued

D-peptide binding and neutralization

| Sample | Sequence | |
|---|---|---|
| R4#6 | ACPIEWRWLCGGGSA | (SEQ ID NO: 21) |
| PhD1 | ACPREWHWLCGGGSA | (SEQ ID NO: 22) |

The term "D-amino acid residue", as used herein, refers to an α-amino acid residue having the same absolute configuration as D-glyceraldehyde. When the amino acid residue includes a first non-hydrogen α-substituent and a second α substituent selected from methyl and halogen, the absolute configuration is the same as that of D-glyceraldehyde with the second α substituent taking the place of the hydrogen atom at the glyceraldehyde α-carbon.

The peptides, portions of the peptides, variations/derivatives of the peptides or portions of the variations/derivatives described herein can be used as inhibitors of HIV entry into cells. The peptides disclosed herein, or a portion of a peptide sufficient to fit into the hydrophobic pocket at the C-terminal end of the coiled-coil and prevent interaction of the C-peptide region with the N-peptide region of gp41 are useful to inhibit HIV infection. A portion of any of the peptides represented or of a derivative thereof can be from 2 to 10 (any number of residues from 2 to 10) amino acid residues in size. D-peptides which comprise the consensus sequence EWXWL (SEQ ID NO: 30) or the sequence WXWL (SEQ ID NO: 31), described herein, and additional residues, can be used; the other residues present in such D-peptides and the size of the D-peptides can be selected with reference to peptides described herein or can be designed independent of those peptides, provided that these three or four residues are positioned in such a manner that the peptide can fit into the hydrophobic pocket and act as an inhibitor. Additional amino acid residues can also be present at the N-terminus, the C-terminus or both of the D-peptides described herein, thus producing a larger peptide. Alternatively, there can be other amino acid residues selected, for example, to enhance binding affinity. Alternatively, a peptide which comprises the conserved amino acid residues of the D-peptides disclosed herein can be used. For example, such a peptide can include the conserved amino acid residues, which can be at the same positions as those at which they occur in the peptides disclosed herein. In one embodiment, the peptide can comprise the core sequence "WXWL" (SEQ ID NO: 31).

The intervening amino acid residues can be different from the amino acid residues at these positions in any of the peptides disclosed herein (e.g., can be isoleucine or asparagine or other amino acid residue which does not appear in the peptides disclosed herein) or can be substituted for or replaced by an amino acid residue represented at a specific position in another peptide. Amino acid residues other than the D-versions of the 20 L-amino acids found in natural proteins can be used. Such changes can be made, for example, to enhance bioavailability, binding affinity or other characteristic of the peptide. A D-peptide can comprise the conserved amino acid residues present in the peptides disclosed herein, but they can be separated by fewer (or more) amino acid residues than the number of intervening amino acid residues shown in Table 1. For example, fewer than five amino acid residues (e.g., Tarrago-Litvak, L. et al., FASEB, J., 8:497 (1994); Tucker, T. J. et al., Methods Enzymol., 275:440 (1996), Tarrago-Litvak, L. et al., FASEB, J., 8:497 (1994); Tucker, T. J. et al., Methods Enzymol., 275:440 (1996)), can be present between the first cysteine and the glutamic acid in the consensus sequence. Alternatively, these two residues can be separated by more than five amino acid residues. Internal modifications can also be made (e.g., to enhance binding or increase solubility of a peptide). For example, the first tryptophan of D10p5 can be replaced by an arginine to increase solubility. A D-peptide can have additional moieties or amino acids at its N-terminus. For example, a moiety which blocks the N terminus or gets rid of the charge otherwise present at the N-terminus can be added. The moiety can be, for example, a blocking moiety, such as an acetyl group linked directly to the glycine (G), or an acetyl group linked to one or more additional amino acid residues linked to the N-terminal of G, such as an acetyl group linked to one or more lysine residues, which, in turn, are linked to the N terminal G. In one embodiment, two lysine residues are linked to the N-terminal G (KKGAC..., SEQ ID NO: 32), for example to increase the solubility of the peptide; a blocking moiety, such as an acetyl group, can be linked to the terminal lysine (acetyl group KKGAC..., SEQ ID NO: 32). In another embodiment, four lysine residues are linked to the N-terminal G. In addition, a D-peptide can have additional and/or altered moieties or amino acids at its C-terminus. For example, one or both of the alanine residues at the C-terminus can be altered and/or one or more residues can be added at the C-terminus, for example to enhance binding. Alternatively, functional (chemical) groups other than amino acid residues can be included to produce an inhibitor of the present invention. For example, these additional chemical groups can be present at the N-terminus, the C-terminus, both termini or internally.

Two or more D-peptides can be linked via an appropriate linker (e.g., a linker of amino acid residues or other chemical moieties) to increase the effectiveness of inhibition. Alternatively, one or more D-peptides can be linked via an appropriate linker to a molecule (drug) that binds to HIV gp120, CD4, CCR5, CXCR4, or a non-pocket region of HIV gp41 to increase the effectiveness of inhibition.

Regarding the nomenclature of the peptides disclosed herein, different families of peptides are referred to as x-mers, where x is considered the number of residues between the cysteine residues. The x-mers are referred to as the "core peptides." For example, SEQ ID NO: 6 (KGACDYPEWQWLCAA) is comprised of 15 residues, and so in the standard art would be referred to as a 15-mer. However, in the present invention, the length of residues between the cysteines (C) is 8, so it would be considered an 8-mer (and referred to as having 8 core residues), and referred to as such throughout the application. This applies to all of the sequences referred to herein. Amino acids outside of the two Cys residues are referred to as "flanking" sequences. This naming scheme allows different families of peptides that differ in the number of residues between the two Cys residues, but can vary in total peptide length due to differences in their flanking sequences, to be distinguished. For example, SEQ ID NO: 6 (KGACDYPEWQWLCAA) has a length of 15 residues, is a member of the 8-mer peptide family (as it has 8 core residues), and has an N-terminal flanking sequence of KGA and a C-terminal flanking sequence of AA. In comparison, SEQ ID NO: 2 (KKGACESPEWRWLCAA) has a total peptide length of 16 residues, but is also a member of the 8-mer peptide family and contains an N-terminal flanking sequence of KKGA and a C-terminal flanking sequence of AA.

As described above, the D-peptides of the present invention can be flanked by GA at the N-terminus and AA at the C-terminus, due to the design of the library used in identifying the D-peptides. Some or all of these four amino acid residues may be altered, replaced or deleted in order to produce D-peptides with, for example, altered absorption, distribution, metabolism and/or excretion. In one embodiment, the C-terminus is modified by the addition of a glycine residue immediately before the C-terminal amide. In another embodiment, the most C-terminal A is altered/modified or replaced by a different amino acid residue or deleted.

D-peptides, which are of the opposite handedness from the handedness of naturally-occurring peptides, do not serve as efficient substrates for enzymes, such as proteases, and, therefore, are not as readily degraded as L-peptides. In addition, there is no effective immune response which targets D-peptides and therefore, they do not elicit an immune response comparable to that elicited by L amino acid peptides.

The peptides disclosed herein can also be present at multimers, such as dimers or trimers. Such multimers are discussed in more detail below. When the multimer is a dimer, the dimer can be comprised of two identical peptides, or can be comprised of two different peptides. The multimer can also be a trimer. When the multimer is a trimer, the trimer can be comprised of two identical peptides and one different peptide, or three identical peptides, or three different peptides, each of which are distinct from each other. The peptides disclosed herein can also be present as pharmaceutical compositions. This is discussed in more detail below.

2. Multimers

As mentioned above, also disclosed are multimers of the peptides which are disclosed herein. The multimer can comprise at least one peptide which interacts with the N-trimer pocket of a viral transmembrane protein. The multimer can be a dimer, trimer, or higher order multiples. The multimers are crosslinked by methods known to those of skill in the art. An example of a crosslinker is PEG derivatized with NHS-ester (reacts with Lys) or maleimide (reacts with Cys). Crosslinkers can also contain two distinct linkage chemistries (e.g., NHS-ester on one end and maleimide on the other end). Peptides may also be linked by direct disulfide bond formation between two Cys residues.

The peptides that are linked can be any of those disclosed herein, and the peptides can be identical to each other or can each be different. When a dimer is present, the N-termini of both of the peptides can be crosslinked to each other. Alternatively, the C-termini of the peptides can be crosslinked. Also, the N-terminus of one peptide and the C-terminus of the other peptide are crosslinked. When a trimer is present, the N-termini and C-termini can be linked in any combination. For example, they can be linked in any of the following arrangements:

N-N/C-C—peptide 1's N-terminus links to peptide 2's N-terminus; peptide 2's C-terminus links to peptide 3's C-terminus. Using this naming, there are 16 possible trimer linages:
X/Y where
X and Y=N-N, N-C, C-N, or C-C The naming scheme for multimers describes the way the peptides are connected. For example, C5C-PIE7-trimer means that three PIE7 peptides are connected via C- to C-terminal connections using a PEG5 spacer. N9C-PIE7-trimer means that three PIE7 peptides are connected via N- to C-terminal connections using a PEG9 spacer. Some examples of dimers are as follows: N9C-PIE7-dimer, C9C-PIE7-dimer, N5N-PIE7-dimer, N5C-PIE7-dimer, C5C-PIE7-dimer, NON-PIE7-dimer, N0C-PIE7-dimer, and C0C-PIE7-dimer. Note: The zero length spacers can be any of a variety of short crosslinkers (e.g., BS3, DSG, or DST). Table 4 contains inhibitory data for these multimers. The structure of DSG is as follows:

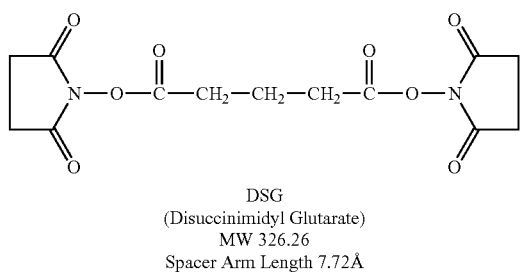 [SMILES: O=C(CCCC(=O)ON1C(=O)CCC1=O)ON1C(=O)CCC1=O]

DSG
(Disuccinimidyl Glutarate)
MW 326.26
Spacer Arm Length 7.72Å

The C5C connection geometry can be used as the preferred linkage for making dimers and trimers. Examples of such dimers include the following: C5C-PIE12-dimer, PEG5-PIE13-dimer (this peptide has an internal Lys residue, and therefore a dimer can be made by crosslinking via this internal Lys). A PEG5 linker can be used, for example. Examples of trimers include: C5C-PIE7-trimer, C5C-PIE12-trimer, and the C0C-PIE7-trimer.

The multimers disclosed herein can be made of any combination of peptides, including those disclosed above in Table 1, or variants thereof. The multimer can be made up of one of the peptides disclosed herein, two of the peptides disclosed herein, or three or more of the peptides disclosed herein. All of the peptides can be identical, or they can be any combination of peptides, including those disclosed and those which are not specifically disclosed. At least one of the peptides can comprise the sequence WXWL (SEQ ID NO: 31), as discussed above. The multimer can inhibit viral entry into a cell. The multimer can be made up of at least one D-peptide, and can comprise all D-peptides, or other components as well.

a) Claw Constructs

As an alternate strategy for making multimers, a central scaffold (such as TSAT, which contains three NHS ester groups) can be used to attach three D-peptides. This geometry is referred to as "the claw", since it looks like an eagle claw. Two examples of this strategy are (1) a short claw (which directly links TSAT to the peptides) and (2) a long claw (which uses an extended form of TSAT (LC-TSAT) that contains an additional six-atom spacer between TSAT and the peptides). Other spacer lengths or compositions (e.g., PEG) can also be used. Examples include PIE7-GK (long claw) and PIE7-GK (short claw).

Below is a representation of LC-TSAT:

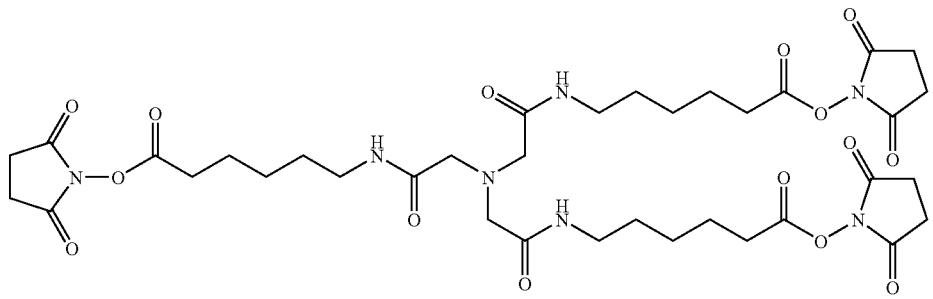 [SMILES: O=C(CN(CC(=O)NCCCCCC(=O)ON1C(=O)CCC1=O)CC(=O)NCCCCCC(=O)ON1C(=O)CCC1=O)NCCCCCC(=O)ON1C(=O)CCC1=O]

And the following is a representation of TSAT:

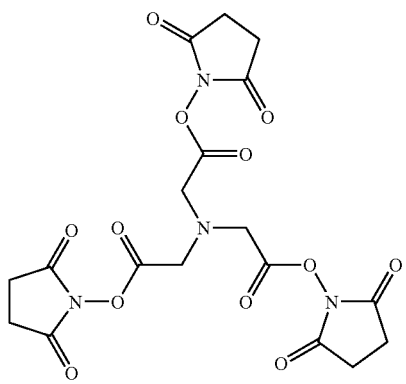 [SMILES: O=C(CN(CC(=O)ON1C(=O)CCC1=O)CC(=O)ON1C(=O)CCC1=O)ON1C(=O)CCC1=O]

b) Avidity of Multimers

The multimers disclosed herein were found to have avidity. As disclosed in Example 1, the dimeric inhibitors PEG-(PIE2-AAA)$_2$ and PEG-(PIE7)$_2$ have IC$_{50}$'s of 21 nM and 1.9 nM (Table 3, FIG. 4), respectively. These values represent a dramatic ~70- and 325-fold improvement over the corresponding monomers. These data also indicate that modest improvements in the potency of monomeric inhibitors are magnified by avidity in the dimer, as also observed in the phage display. The potency of PEG-(PIE7)$_2$ is comparable to Fuzeon (Table 3). The improved potency of the dimers cannot be attributed to an interaction of the PEG with virus, cells, or the D-peptide, but is a genuine avidity effect caused by two D-peptides binding to the N-trimer.

Disclosed herein are compositions comprising a multimer as disclosed herein and an N-trimer molecule, wherein the multimer, when associated with the N-trimer molecule, has an increased affinity for the N-trimer molecule, when compared with the affinity of a single peptide for the N-trimer molecule. The single peptide, or control peptide, can identical to one of the components of the multimer, or the peptide can be a different peptide which is not contained in the multimer.

Also disclosed herein is a composition comprising a multimer as disclosed herein and an N-trimer molecule, wherein the multimer, when associated with the N-trimer molecule, has enhanced antiviral activity when compared with the antiviral activity of a single peptide.

The multimer can exhibit about a 1-fold, 2-fold, 3-fold, 4-fold, 5-fold, 10-fold, 20-fold, 25-fold, 30-fold, 40-fold, 50-fold, 100-fold, 200-fold, 300-fold, 400-fold, 500-fold, 1000-fold, 2000-fold, 3000-fold, 4000-fold, 5000-fold, or 10,000-fold increase in affinity for the N-trimer when compared with the affinity of one of the components of the multimer alone.

The multimer can have any of the characteristics or properties that are disclosed above. Any of the multimers disclosed herein are capable of having avidity as described herein, and any of them can be used with the methods disclosed herein for increasing inhibition of viral entry.

c) Resistance Capacitor

Over-engineering future D-peptides can improve affinity even after reaching the potency limit. Such inhibitors do not show improved potency, but have a reserve of binding energy that acts as a "resistance capacitor" to defend against potential resistance mutations (i.e., resistance mutations that moderately affect binding would have no effect on potency). Of particular importance, this property discourages the stepwise accumulation of multiple subtle mutations that combine to confer resistance. Individual mutations have no effect on inhibitor potency and do not confer a growth advantage in the presence of inhibitors. This resistance capacitor is especially beneficial for trimeric inhibitors, because resistance mutations simultaneously affect all three pockets. As a further defense against the development of resistance, the trimeric D-peptides disclosed herein can also be constructed by using three different D-peptide sequences, each with a distinct resistance profile. Such a heterotrimer would present a significant additional barrier to the development of resistance. (In Welch et al. Proc Natl Acad Sci USA. 2007 Oct. 23; 104(43):16828-33).

A given trimer's potency against HXB2 did not improve as much as expected from its KD (Example 1), which shows that trimer potency against HXB2 may have reached a potency limit imposed by association kinetics. This kinetic limitation is consistent with the short (10-20 min) lifetime of the exposed N-trimer in the gp41 prehairpin intermediate, similar to the time required for binding of the peptides at mid to high pM concentrations.

This HXB2 association kinetics limitation doesn't allow for one to measure if a new inhibitor is better than an earlier one. Instead, JRFL inhibition data can be used, since this virus is much harder to inhibit and requires a much better inhibitor to reach its potency plateau. This is why Table 4 lists JRFL values in addition to HXB2. For example, C5C-PIE7-trimer and N9N-PIE7-trimer have similar IC50 values against HXB2 (already at the limit), but against JRFL there is a ~35-fold difference in potency.

d) Peptide Variants

As discussed herein there are numerous variants of the peptides disclosed herein that are herein contemplated. Peptide variants and derivatives are well understood to those of skill in the art and in can involve amino acid sequence modifications. Those peptides disclosed herein that can be used to inhibit viral entry can comprise such amino acid sequence modifications. One of skill in the art would be able to readily determine which modifications can be made in order to retain the activity of the peptide.

Analogs of the peptides disclosed herein are also contemplated. These analogs include one or more D-amino acids of the peptidic structure which are substituted with a homologous amino acid such that the properties of the original peptide are maintained. Preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g, glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Non-limiting examples of homologous substitutions that can be made in the peptidic structures of the peptides disclosed herein include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain. This is given as an example and is not intended to be limiting. One of skill in the art would be capable of making conservative substitutions to a D-peptide.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence The opposite stereo-isomers of naturally occurring peptides are disclosed, as well as the stereo-isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185

(1979) (—CH₂NH—, CH₂CH₂—); Spatola et al. Life Sci 38:1243-1249 (1986) (—CHH₂—S); Hann J. Chem. Soc Perkin Trans. 1307-314 (1982) (—CH═CH—, cis and trans); Almquist et al. J. Med. Chem. 23:1392-1398 (1980) (—COCH₂—); Jennings-White et al. Tetrahedron Lett 23:2533 (1982) (—COCH₂—); Szelke et al. European Appln, EP 45665 CA (1982): 97:39405 (1982) (—CH(OH)CH₂—); Holladay et al. Tetrahedron. Lett 24:4401-4404 (1983) (—C(OH)CH₂—); and Hruby Life Sci 31:189-199 (1982) (—CH₂—S—); each of which is incorporated herein by reference. A particularly preferred non-peptide linkage is —CH₂NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by proteases and peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

3. Pharmaceutical Carriers/Delivery of Pharmaceutical Products

As described above, the peptides and multimers disclosed herein (alternatively referred to as compositions) can also be administered in vivo in a pharmaceutically acceptable carrier. By "pharmaceutically acceptable" is meant a material that is not biologically or otherwise undesirable, i.e., the material may be administered to a subject, along with the peptide disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disease, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

a) Pharmaceutically Acceptable Carriers

The compositions, including peptides and multimers thereof, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed peptides and multimers thereof can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions such as peptides and multimers thereof may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products, particularly for D-peptides. Examples of such guidance can be found throughout the literature. For example, the peptide Fuzeon, which has been FDA approved, can act as a guide for the dosages required for the peptides disclosed herein. In one embodiment, the typical daily dosage of the peptides or multimers thereof used alone might range from about 1 µg/kg to up to 100 mg/kg of body weight or more per day, depending on the factors mentioned above. Furthermore, the peptides disclosed herein can be administered several times daily, daily, weekly, monthly, or yearly, depending on the condition of the subject, other modes of therapy, etc. One of skill in the art could readily ascertain an appropriate dosing schedule.

Following administration of a disclosed composition, such as an antibody, for treating, inhibiting, or preventing a viral infection, such as HIV, the efficacy of the peptide or multimer thereof can be assessed in various ways well known to the skilled practitioner. For instance, one of ordinary skill in the art will understand that a composition, such as a D-peptide, disclosed herein is efficacious in treating or inhibiting a viral infection in a subject by observing that the composition inhibits viral entry. Efficacy of the administration of the disclosed composition may also be determined by measuring the number of uninfected cells in the infected subject. A treatment that inhibits an initial or further decrease in uninfected cells in a subject or patient, or that results in an increase in the number of uninfected cells in, for example, the HIV-positive subject, is an efficacious treatment. The efficacy can also be evaluated using indirect measures of infection, such as CD4+ cell counts, levels of anti-virus antibodies, and PCR to detect viral RNA levels.

The compositions that inhibit viral entry, i.e., microbicides, disclosed herein may be administered prophylactically to patients or subjects who are at risk for being exposed to a virus such as HIV or who have been newly exposed to HIV. In subjects who have been newly exposed to a virus such as HIV but who have not yet displayed the presence of the virus (as measured by PCR or other assays for detecting the virus) in blood or other body fluid, efficacious treatment with a peptide or multimer thereof partially or completely inhibits the ability of the virus to infect cells.

The disclosed compositions and methods can also be used for example as tools to isolate and test new drug candidates for a variety of viral-related diseases.

4. Chips and Micro Arrays

Disclosed are chips where at least one address is the sequences or part of the sequences set forth in any of the peptide sequences disclosed herein.

Also disclosed are chips where at least one address is a variant of the sequences or part of the sequences set forth in any of the peptide sequences disclosed herein.

5. Computer Readable Mediums

It is understood that the disclosed peptides can be represented as a sequence consisting of the amino acids. There are a variety of ways to display these sequences, for example the amino acid valine can be represented by Val or V. Those of skill in the art understand how to display and express any peptide sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the peptide sequences are recorded, stored, or saved.

6. Compositions Identified by Screening with Disclosed Compositions/Combinatorial Chemistry a) Combinatorial Chemistry The disclosed peptides can be used as targets for any combinatorial technique to identify molecules or macromolecular molecules that interact with the disclosed compositions in a desired way. The peptides and related molecules disclosed herein can be used as targets for the combinatorial approaches. Also disclosed are the compositions that are identified through combinatorial techniques or screening techniques in which the compositions disclosed in SEQ ID NOS: 1-29 for example, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation of gp41 interactions. The molecules identified and isolated when using the disclosed compositions, such as other peptides, are also disclosed. Thus, the products produced using the combinatorial or screening approaches that involve the disclosed compositions, such as peptides, are also considered herein disclosed.

It is understood that the disclosed methods for identifying molecules that inhibit viral entry, for example, can be performed using high throughput means. The methods for screening are discussed in more detail below.

b) Computer Assisted Drug Design

The disclosed peptides and multimers thereof can be used as targets for any molecular modeling technique to identify either the structure of the disclosed peptides or multimers or to identify potential or actual molecules, such as small molecules, which interact in a desired way with the disclosed compositions. The peptides and related molecules disclosed herein can be used as targets in any molecular modeling program or approach.

It is understood that when using the disclosed compositions in modeling techniques, molecules, such as macromolecular molecules, will be identified that have particular desired properties such as viral inhibition. The molecules identified and isolated when using the disclosed compositions, such as peptides and multimers thereof, are also disclosed. Thus, the products produced using the molecular modeling approaches that involve the disclosed compositions are also considered herein disclosed. A molecular model for gp41 is discussed in more detail in Example 1.

Generally, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

7. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a pharmaceutical composition comprising a peptide or multimer thereof as disclosed herein. For example, disclosed is a kit for treating HIV, comprising a pharmaceutical composition comprising a peptide or multimer thereof as disclosed herein.

8. Compositions with Similar Functions

It is understood that the peptides disclosed herein have certain functions, such as inhibiting viral entry. Disclosed herein are certain structural requirements for performing the disclosed functions, and it is understood that there are a variety of structures which can perform the same function which are related to the disclosed structures, and that these structures will ultimately achieve the same result, for example inhibiting viral entry.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Peptide Synthesis

The peptides disclosed herein can be linked, for example, by disulfide crosslinks. For example, the D-peptides disclosed herein have two Cys residues connected by a disulfide bond, which circularizes the peptide and creates a more compact and structured peptide. This disulfide is known to have enhanced antiviral properties. There are many alternative methods for circularizing peptides known to those of skill in the art. For example, a peptide can be circularized using lactam or other chemical bridges, PEG or other chemical crosslinkers, peptide ligation, or selenocysteine disulfides.

Two or more peptides or polypeptides can also be linked together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry N. Academic Press, New York, pp. 257-267 (1992)).

E. METHODS OF USING THE COMPOSITIONS

1. Methods of Using the Compositions as Research Tools

Disclosed herein are methods for evaluating the ability of a composition comprising a peptide of less than 10 core residues in length for its ability to inhibit viral entry into a cell comprising: incubating the composition and a cell under conditions sufficient to allow the components to interact; contacting the components with a virus; and evaluating the ability of the composition to inhibit viral entry into the cell. The peptide can comprise less than 7, 8, 9, or 10 core amino acid residues. The peptide can be present as a multimer, as disclosed above. The composition can inhibit viral entry by interacting with a viral transmembrane protein, such as HIV gp41. The peptide can be a D-peptide. Furthermore, evaluating the ability of the composition to inhibit viral entry can be by detection of a reporter means. Examples of such reporter means include, but are not limited to, a radioisotope, a fluorescent compound, a bioluminescent compound, a chemiluminescent compound, a metal chelator, or an enzyme. Evaluating the ability of the composition to inhibit viral entry into the cell can be done by evaluating the ability of the composition to be displaced from its binding site (the gp41 N-trimer pocket) by other compounds (e.g., peptides, small molecules, nucleic acids, natural products). By "displaced" is meant that the composition is inhibited from binding, or is disrupted from its interaction with the binding site. This can occur at 5, 10, 15, 20, 25, 30, 35, 40, 45, 50, 55, 60, 65, 70, 75, 80, 85, 90, 95, or 100% displacement of the test compositions from the binding site.

The ability of the composition to inhibit viral entry can be measured using viral entry assays or cell-cell fusion assays. Viral entry assays are known to those in the art, as are cell-cell fusion assays. One can use a displacement assay comprising other compounds that can displace the test composition from the binding site. Examples include, but are not limited to, peptides, small molecules, nucleic acids, or natural products. Such displacement assays are known to those of skill in the art.

Also disclosed is a method of identifying a multimer with increased affinity for an N-trimer molecule when compared with the affinity of one of a single peptide, comprising: incubating the multimer and an N-trimer molecule; measuring the affinity of the multimer for the N-trimer molecule; and comparing the affinity of the multimer for the N-trimer molecule with the affinity for the N-trimer molecule of a single peptide.

Further disclosed is a method of identifying a multimer with enhanced antiviral activity for an N-trimer molecule when compared with the antiviral activity of one a single peptide, comprising: incubating the multimer with a cell; contacting the components of step (a) with a virus; measuring the antiviral activity of the multimer; and comparing the antiviral activity of the multimer with the antiviral activity of a single peptide. The single peptide can be identical to one of the components of the multimer, or can be different. The multimer can comprise at least one peptide which interacts with the N-trimer pocket of viral gp41.

Inhibition of complex formation of gp41 can be assessed by determining the extent to which binding of the two members of the complex occurs, such as by means of a fluorescence assay (e.g., FRET), in which C34 and N36 are each labeled by a member of a pair of donor-acceptor molecules or one end of one of the peptides (e.g., the N-terminus of C34) is labeled with one member of such a pair (EDANS) and the natural fluorophore tryptophan, present in the N36 peptide, is the other member of the donor/acceptor pair. Binding of the C34 and N36 is assessed by the extent to which light emission (FRET) occurs from the acceptor model and/or the wavelength spectrum of the light emitted is altered. Prevention of binding by the candidate drug alters the extent to which light is emitted and/or prevents the shift in wavelength that would occur if binding of C34 and N36 occurred. Alternatively, C34 can be labeled with a detectable label, such as a radiolabel (e.g., by synthesizing a variant C34 with a kinase recognition site that can be labeled with a kinase and radioactive ATP). The radiolabeled C34 and the candidate drug are combined with N36 immobilized to, for example, a solid surface (e.g., a bead or a plastic well), thus producing a test sample. The extent to which binding of labeled C34 with immobilized N36 occurs is determined and compared with the extent to which binding of labeled C34 to immobilized N36 occurs under the same conditions to which the test sample is subjected, but in the absence of the candidate drug (in a control sample). Typically, this assessment is carried out after the sample has been maintained for sufficient time and under appropriate conditions for C34/N36 binding to occur and a subsequent wash to remove any unbound C34 and candidate drug. If binding occurs in the test sample to a lesser extent than in the control sample, as evidenced by less radiolabel bound to the immobilized N36 in the test sample than in the control sample, the candidate drug is an inhibitor of binding of C34 and N36. Alternatively, the label or tag on C34 can be a member of a binding pair, the other member of which is used to detect binding to N36. For example, C34 can be tagged with biotin (through standard solid-state peptide synthesis, for example) and combined with N36, which can be in solution or bound to a solid surface, such as a bead, well or flat/planar surface, along with the candidate drug (test sample) or in the absence or the candidate drug (control sample). Binding of C34 to N36 is assessed by detecting the presence of biotin associated with N36, such as through the use of labeled streptavidin (e.g., streptavidin-HRP, streptavidin-AP or iodinated streptavidin), which binds the biotin on C34 and is then itself detected through its label. If binding occurs less in the presence of the candidate drug (in the test sample) than in the absence of the candidate drug (in the control sample), as indicated by the presence of less biotin detected on N36 in the test sample than in the control sample, the candidate drug is an inhibitor of C34/N36 binding. The candidate drugs can be obtained, for example, from a library of synthetic organic compounds or random peptide sequences, which can be generated synthetically or through recombinant technology.

In a similar fashion, the ability of a candidate drug to disrupt C34/N36 binding can be assessed, to identify inhibitors of C34/N36 and, thus, of HIV infection. In this embodiment, preformed C34/N36 complex is combined with a candidate drug, which is to be assessed for its ability to disrupt the complex, thus producing a test sample. The control sample is the same as the test sample, except that the control sample does not contain the candidate drug; it is treated in the same manner as the test sample. If C34/N36 binding is disrupted in the presence of the candidate drug and not in the control sample or if disruption of the complex occurs to a greater extent in the test sample than in the control sample, the candidate drug is an inhibitor (disrupter) of C34/N36. Detection of disruption of binding can be carried out as described above for detection of/prevention of/interference with binding of C34/N36 (e.g., by FRET or a fluorescence assay, by detecting a radiolabel or other detectable label, such as biotin.)

In another embodiment, the invention relates to a method of identifying a drug that binds the N-helix coiled-coil cavity of HIV gp41. Here, too, the assay is based on assessing loss or decrease in binding, but unlike the C34/N36 complex assay described above, which is a more general assay in that it covers or detects interaction with any portion of the groove formed by the N-helical region of HIV gp41, this embodiment focuses on the HIV gp41 hydrophobic pocket (the N-helix coiled-coil cavity). In this embodiment, the method comprises combining a candidate drug to be assessed for its ability to bind the N-helix coiled-coil cavity of HIV gp41 with a fusion protein that comprises a trimeric version of the coiled-coil region of a protein and a sufficient portion of the N-peptide of HIV gp41 to include the HIV gp41 cavity, under conditions appropriate for presentation of the HIV gp41 cavity for binding by a peptide or other molecule and determining (e.g., in a high throughput screen) whether the candidate drug binds the fusion protein. If binding occurs, the candidate drug is a "hit" that may be a drug that binds the N-helix coiled-coil cavity of HIV gp41. If binding occurs, the candidate drug has bound the N-helix coiled coil and it can be determined if it binds to the coiled-coil cavity. Such "hits" can then be screened in secondary assays, such as the cell/cell fusion assay and HIV infectivity assay to determine if the candidate drug is a drug. Alternatively, or in addition, such "hits" can be assessed further by use of a counterscreen with other fusion proteins (or peptides), to which pocket-binding molecules will not bind.

In a further embodiment, a competitive assay is carried out. In this embodiment, a peptide or protein that binds the N-helix coiled-coil cavity of HIV gp41 is combined with the candidate drug and the fusion protein and whether the candidate drug binds the HIV gp41 cavity is determined in the presence of the peptide that binds the N-helix coiled cavity of HIV gp41. If the candidate drug binds the fusion protein, it is a drug that binds the HIV gp41 cavity. For example, a fusion protein which comprises a trimeric version of the coiled-coil region of GCN4 and the C-terminus of the N peptide of HIV gp41 that includes the N-helix coiled-coil cavity (IQN17) is combined with a "reference" D-peptide (e.g., any of the D-peptides described herein or variants thereof) that binds the N-helix coiled-coil cavity and a candidate drug to be assessed for its ability to bind the N-helix coiled-coil cavity of HIV gp41, thus producing a test sample, which is maintained under conditions appropriate for binding of the D-peptide to bind to the cavity. A control sample, which includes the same components as the test sample, except for the candidate drug, and is handled in the same manner as the test sample, is also assessed. In both samples, binding of the reference D-peptide is assessed. If binding of the reference D-peptide occurs to a lesser extent in the presence of the candidate drug (in the test sample) than in its absence (in the control sample), the candidate drug is a drug that binds the N-helix coiled-coil cavity of HIV gp41. Detection of binding is assessed, for example, in a similar manner as described above for the C34/N36 embodiment of the invention. For example, the D-peptide is labeled with a detectable label, such as a radiolabel or a first member of a binding pair (e.g., biotin), and the extent to which the N-helix coiled-coil cavity bears the label (after the samples have been maintained under conditions appropriate for binding of the reference D-peptide to the cavity) is determined. In the case in which radiolabeling is used, the extent to which the fusion protein bears the radiolabel is assessed in the test sample and compared with the extent to which the fusion protein bears the radiolabel in the control sample. If the detectable label is a first member of a binding pair (e.g. biotin), the second member of the pair (a binding partner) is added to the samples in order to detect the extent to which the fusion protein is bound by the reference D-peptide. This can be done directly or indirectly (e.g., by adding a molecule, such as an antibody or other moiety which binds the second member of the binding pair). Less of the label will be present on the fusion protein (N-helix coiled-coil cavity) if the candidate drug has inhibited (totally or partially) binding of the D-peptide to the cavity. If binding occurs to a lesser extent in the test sample (in the presence of the candidate drug) than in the control sample (in the absence of the candidate drug), then the candidate drug is a drug that binds the N-helix coiled-coil cavity of HIV gp41.

IQN17, or a variant thereof, in the D-enantiomer, is useful to identify molecules or compounds which are members of a library or collection and bind the N-helix coiled-coil of gp41. For example, a library or collection of molecules or compounds, such as a phage display library, can be screened with IQN17 in the D-enantiomer to identify members that bind the pocket. This has been carried out successfully, as described herein. The mirror image of IQN17, or a variant thereof, is used as the target molecule. As used herein, the terms "D-enantiomer of a polypeptide" and "D-peptide" refer to the exact mirror image of the molecule in the natural handedness. Thus, for amino acid residues that contain a second chiral center, such as Ile and Thr, the exact mirror image of the naturally-occurring amino acid residue is used to create the D version of the polypeptide. Also as used herein, the terms "D-amino acids" and "L-amino acids" are both meant to include the non-chiral amino acid glycine. D-IQN17 can be immobilized to a solid surface, such as by addition of one member of a binding pair (e.g., biotin) to it and addition of the other member of the pair (e.g., streptavidin) to the solid surface. Binding of the two members results in immobilization of D-IQN17 on the solid surface, such as for phage panning. A linker which is an enzyme recognition site (e.g., an amino acid linker such as Gly-Lys-Gly, in which an L-lysine residue is used) can be placed between the D-IQN17 sequence and the binding pair member (between the biotin and D-IQN17) to provide an enzyme recognition site (here, a trypsin recognition site), so that bound phage can be eluted by a trypsin digestion, rather than by non-specific elution, such as acid addition. The phage display library can be a library of L-amino acid peptides of any appropriate length fused to an appropriate phage gene. In one embodiment, it is a phage display library of L-amino acid peptides fused to the gIII gene of M13 phage. The peptides, in one embodiment, comprise 10 randomly encoded amino acid residues flanked by either a cysteine or a serine on both sides. Typically, several rounds of panning are carried out. D-IQN17-specific binding phage are identified. Phage that bind only the gp41 region of D-IQN17 can be identified by post-panning assessment, such as by screening against wells that lack the antigen and then further testing against a panel of molecules. For example, specific pocket-binding phage include those that bind D-IQN17 but not D-GCN4-pI.sub.QI (with the same three surface mutations as in IQN17) or a version of D-IQN17 with a point mutation in the hydrophobic pocket, D-IQN17(G39W), in which glycine 39 is mutated to tryptophan, resulting in a large protrusion into the pocket. D-peptides identified in this manner can be assessed for their ability to inhibit HIV gp41, using known assays, such as the cell/cell fusion assay and HIV infectivity assay. The mirror-image phage display method described herein has demonstrated the value of IQN17 and IQN17(G39W), and their D-enantiomers in identifying inhibitors of HIV-1 entry that bind the gp41 pocket. Of nine specific pocket-binding phage sequences identified (phage that bind to D-IQN17 but not to D-IQN17(G39W), eight contain a consensus EWXWL sequence and inhibit HIV-1 gp41-induced syncytia formation when tested as D-peptides. The ninth peptide was toxic to cells and was not investigated further.

The D-versions of IQN17 and IQN17(G39W) can be used in a similar manner with other biologically encoded libraries, to discover other pocket-binding molecules that are not subject to enzymatic degradation by natural enzymes. For example, other phage-display libraries can be used to identify new D-peptide inhibitors (e.g., with a different number of residues between the flanking Cys residues and/or with randomly encoded amino acid residues outside the regions flanked by cysteine residues and/or with more than two cysteine residues). Strategies for encoding peptide libraries without phage (e.g., in which the encoding mRNA is attached to the peptide) can be used to identify D-peptide inhibitors. RNA or DNA libraries can be used (e.g., with SELEX methods) to identify L-ribose- or L-deoxyribose-based RNA or DNA aptamers, respectively, that bind to the hydrophobic pocket and are not substrates for natural nucleases (see e.g., Williams et al., PNAS, 74:11285 (1997)).

Although the versions of IQN17 and IQN17(G39W) of natural L-handedness can also be used in similar manner with biologically encoded libraries, the most likely applications will be with other, non-biologically encoded libraries. For example, chemical combinatorial libraries on beads (of the one-bead, one-compound variety) can be screened with labeled IQN17 (e.g., radioactive or with a chromophore) to identify beads containing molecules that bind to IQN17. In this example, IQN17(G39W) can be used as a counterscreen to determine if the molecules on the bead bind to the pocket of IQN17. (If they bind to IQN17(G39W), then they are not likely to be pocket-binding molecules.) As another example, beads to which IQN17 had been previously attached can be incubated with a mixture of potential pocket-binding molecules (e.g., a mixture of chemicals, or a natural product extract). IQN17 (bound to the beads) can then be separated from the mixture, washed, and then subjected to conditions (e.g., organic solvent, low pH, high temperature) that elute molecules bound to the IQN17 on the beads. The eluted molecules (i.e., potential pocket-binding molecules) could be identified by analytical chemistry methods (e.g., HPLC, mass spectrometry). A counterscreen with IQN17(G39W) is useful to help to identify true pocket-binding molecules.

Drugs identified by the methods described above are then further tested for their ability to inhibit (totally or partially) HIV gp41 function (membrane fusion) and, thus entry into cells, using further in vitro assays, such as the syncytium assays and/or infectivity assays described herein or others known to those of skill in the art, and/or in vivo assays in appropriate animal models or in humans.

One embodiment of the present invention is a method of identifying a drug that binds the N-helix coiled-coil of HIV gp41, particularly the N-helix coiled-coil pocket. The method comprises combining a candidate drug to be assessed for its ability to bind the N-helix coiled-coil pocket of HIV gp41 and peptide which comprises a soluble, trimeric coiled-coil and a sufficient portion of the N-peptide of HIV gp41 to include the HIV gp41 pocket, under conditions appropriate for presentation of the HIV gp41 pocket for binding by a molecule or compound (e.g., a drug) and determining whether the candidate drug binds the HIV gp41 pocket. If binding of the candidate drug with the HIV gp41 pocket occurs, the candidate drug is a drug which binds the N-helix coiled-coil pocket of HIV gp41. Optionally, binding of the candidate drug can be assessed in the assay as described above, except that a peptide that binds the N-helix coiled-coil pocket (a peptide previously identified as one which binds the pocket) is combined with the candidate drug and the peptide. In this competitive assay, binding of the candidate drug to the N-helix coiled-coil pocket is assessed in the presence of a known binding moiety (a molecule or compound which binds the pocket). If binding of the candidate drug occurs in the presence of the known binding moiety, the candidate drug is a drug which binds the N-helix coiled-coil pocket with sufficient affinity to successfully compete with the known binding moiety. The fusion protein used in this embodiment comprises a soluble, trimeric version of a coiled-coil, such as a soluble, trimeric version of the coiled-coil region of a protein and a sufficient portion of the N-peptide of HIV gp41 to include the HIV gp41 cavity. Alternatively, a variant of the HIV gp41 sequence present herein, a sequence from another strain of the human virus (e.g., HIV-2) or a sequence from another species (e.g., SIV, feline immunodeficiency virus, Visna virus (M. Singh et al., J. Mol. Biol., 290:1031 (1999)) can be used in the fusion protein or soluble model. The fusion protein can comprise a soluble, trimeric version of the coiled-coil of any protein, provided that when it is in the fusion protein with the HIV component, the HIV cavity is presented in such a manner that it is available for binding. It can be, for example, that of GCN4-pIQI, GCN4-pII, Moloney Murine Leukemia Virus (Mo-MLV) or the ABC heterotrimer. In one embodiment, the fusion protein is IQN17 in the D-form. In another embodiment, the fusion protein is IQN17 in the natural L-handedness.

In the competitive assay format, any peptide known to bind the N-helix coiled-coil cavity can be used as the known binding moiety. For example, any of the peptides described herein or a variant or portion thereof can be used. Also, any non-peptide pocket-binding molecule can be used in the competitive assay format. The competitive assay can be performed in solution, on a bead, or on a solid surface.

In one embodiment, the candidate drug is detectably labeled and binding of the candidate drug to the HIV gp41 N-helix coiled-coil is determined by detecting the presence of the detectable label on the HIV gp41 N-helix coiled-coil (as a result of binding of the labeled candidate drug to the N-helix coiled-coil). Detection of the label on the helix coiled-coil pocket of the soluble model is indicative of binding of the candidate drug to the N-helix coiled-coil pocket and demonstrates that the candidate drug is a drug which binds the N-helix coiled-coil pocket. If the labeled candidate drug is detected on the fusion protein, the candidate drug is a drug which binds the N-helix coiled-coil cavity.

In another embodiment of the method of identifying a drug that binds the N-helix coiled-coil pocket of the HIV gp41, a soluble model that presents the pocket in such a manner that it is available for binding by a drug is combined with a candidate drug and whether binding of the candidate drug with the N-helix coiled-coil of the soluble model occurs is determined. If binding occurs, the candidate drug is a drug which binds the pocket. Here, too, a competitive assay format can be used. The components of the competition assay (e.g., IQN17 and a D-peptide) can be labeled, with any of a variety of detectable labels, including fluorophore/quencher combinations. The candidate drug can be labeled, as described above, with any of a variety of detectable labels. The components of the soluble model (fusion protein) used in this embodiment and the competing moiety which is used in a competitive assay format can also be as described above.

The present invention also relates to a method of producing a drug that binds the N-helix coiled-coil pocket of HIV gp41. In one embodiment, the method is carried out as follows: A soluble model that presents the N-helix coiled-coil pocket of HIV gp41 or a fusion protein which comprises a soluble, trimeric coiled-coil is combined with a candidate drug to be assessed for its ability to bind the N-helix coiled-coil pocket of HIV gp41 and inhibit entry into cells, under conditions appropriate for presentation of the HIV gp41 pocket for binding by a drug. Whether the candidate drug binds the HIV gp41 pocket is determined, wherein if binding of the candidate drug to the N-helix coiled-coil pocket of HIV gp41 occurs, the candidate drug is a drug which binds the N-helix coiled-coil cavity of HIV gp41. In this embodiment, the fusion protein comprises a soluble, trimeric coiled-coil and a sufficient portion of the N-peptide of HIV gp41 to include the HIV gp41 N-helix coiled-coil pocket IQN17, described herein, can be used in this method; the D enantiomer of IQN17 can also be used (e.g., in mirror-image phage applications). The ability of the drug produced to inhibit HIV entry into cells is assessed, for example, in a syncytium assay and/or an infectivity assay, as described herein. It can be further assessed in an appropriate animal model or in humans.

Also disclosed herein is a method of producing a drug that binds the N-helix coiled-coil pocket of HIV gp41. The method comprises: producing or obtaining a soluble model of the N-helix coiled-coil pocket of HIV gp41; combining a candidate drug (a molecule or compound) to be assessed for it ability to bind the N-helix coiled-coil pocket of HIV gp41 and the soluble model of the N-helix coiled-coil pocket of HIV gp41 and determining whether the candidate drug binds the N-helix coiled-coil pocket of HIV gp41. If the candidate drug binds the N-helix coiled-coil pocket of HIV gp41, the candidate drug is a drug which binds the N-helix coiled-coil pocket of HIV gp41; as a result, a drug which binds the N-helix coiled-coil cavity of HIV gp41 is produced. The fusion protein used in this embodiment is described herein and can be, for example, IQN17, the D enantiomer of IQN17, or variants thereof. Alternatively, a drug that binds the N-helix coiled-coil pocket of HIV gp41 and inhibits entry of HIV into cells can be produced by a method comprising: producing or obtaining a soluble model of the N-helix coiled-coil pocket of HIV gp41, as described herein; combining the soluble model and a candidate drug to be assessed for its ability to bind the N-helix coiled-coil pocket of HIV gp41; determining whether the candidate drug binds the N-helix coiled-coil pocket of the soluble model (fusion protein), wherein if binding occurs, the candidate drug is a drug which binds the N-helix coiled-coil of HIV gp41; and assessing the ability of the drug which binds the N-helix coiled-coil to inhibit HIV entry into cells, wherein if the drug inhibits HIV entry into cells, it is a drug which binds the N-helix coiled-coil pocket of HIV gp41 and inhibits HIV entry into cells. Its ability to inhibit HIV entry into cells can be assessed in vitro (e.g., in a syncytium assay, an infectivity assay) or in vivo (e.g. in an appropriate animal model or in humans). The soluble model can be a peptide which comprises a soluble, trimeric coiled-coil, such as that of a protein and a sufficient portion of the N-peptide of HIV gp41 to include the HIV gp41 pocket.

Drugs identified or produced by the methods described herein, as well as by other methods, which bind the N-helix coiled-coil pocket of HIV gp41 and inhibit HIV entry into cells are also the subject of this invention.

Drugs identified or produced by the methods described herein, as well as by other methods, which bind to more than one N-helix coiled-coil pocket of HIV gp41 and inhibit HIV entry into cells are also the subject of this invention. Such drugs can be obtained, for example, by linking two or more pocket-binding molecules (drugs) via an appropriate linker (e.g., a linker of amino acid residues or other chemical moieties) to increase the effectiveness of inhibition. The pocket-binding molecules that are linked can be the same or different. Drugs identified or produced by the methods described herein or by other methods which bind to the N-helix coiled-coil pocket of HIV gp41, in addition to binding to HIV gp120, CD4, CCR5, CXCR4, or a non-pocket region of HIV gp41 are also the subject of this invention.

Drugs which inhibit HIV gp41 can also be designed or improved with reference to the X-ray crystal structure of the complex IQN17 and 2K-PIE1, which is presented herein. Alternatively, or in addition, drugs which inhibit HIV gp41 can also be designed or improved with reference to the X-ray crystal structure of free IQN17, presented herein.

Compounds and molecules (drugs) identified as described herein inhibit (partially or totally) entry of HIV into cells, and thus are useful therapeutically in uninfected individuals (humans) and infected individuals (e.g., to prevent or reduce infection in an uninfected individual, to reduce or prevent further infection in an infected individual) and as research reagents both to study the mechanism of gp41 induced membrane fusion and to assess the rate of viral clearance by an individual and as reagents to discover or develop other compounds and molecules (drugs) that inhibit entry of HIV into cells. D-peptides described herein (e.g., D10pep5, D10pep1) have been shown, using the infectivity assay described herein, to inhibit infection of cells. Other D-peptides can be similarly assessed for their ability to inhibit infectivity.

As disclosed above, putative inhibitors can be identified using Fluorescence Resonance Energy Transfer (FRET) to quickly identify interactions. The underlying theory of the techniques is that when two molecules are close in space, i.e., interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

Using methodology well known to those of skill in the art, in combination with various combinatorial libraries, one can isolate and characterize those small molecules which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes. The disclosed peptides can be used in a variety of ways as research tools. For example, the disclosed peptides, such as SEQ ID NOS: 1-22 can be used to study gp41, by for example acting as inhibitors of viral entry or of proper folding of the protein.

2. Methods of Inhibiting Viral Entry

Disclosed herein is a method for inhibition of transmission of a virus to a cell, or inhibiting viral entry, comprising exposing the virus to a peptide as disclosed herein, thereby inhibiting transmission of the virus to the cell. The virus can be HIV. The peptide can be in a pharmaceutical composition. Also disclosed are methods of administering a pharmaceutical composition.

The methods disclosed herein can be used in conjunction with other viral therapies or antiviral agents. One of more of these antiviral agents can be used, and they can be administered before, during, or after treatment with the compositions disclosed herein. For example, in ongoing therapy, the subject can be administered the compositions comprised herein simultaneously with other treatments, meaning they can be administered about 48 hours, 24 hours, 12 hours, 8 hours, 4 hours, 2 hours, 1 hour, 30 minutes, 20 minutes, 10 minutes, 5 minutes, or one minute before treatment with the disclosed compositions. Other methods of treatment can also be administered before treatment with the compositions disclosed herein. By "before treatment" is meant that another form of treatment was given and then stopped before the current therapy was administered, or could be given immediately before, then administered again afterwards. In this case, the other methods of antiviral therapy can be administered years, months, weeks, days, hours, or minutes in advance. Other methods of treatment can also be administered after treatment with the compositions disclosed herein. By "after treatment" is meant that another form of treatment is administered after the current therapy was administered, or could be given before, then administered again afterwards. This additional antiviral treatment could be given years, months, weeks, days, hours, or minutes after the current therapy is given.

The further antiviral agent or agents can be selected from the group consisting of a viral replication inhibitor, a viral protease inhibitor, a viral reverse transcriptase inhibitor, a viral entry inhibitor, a viral integrase inhibitor, a viral Rev inhibitor, a viral Tat inhibitor, a viral Nef inhibitor, a viral Vpr inhibitor, a viral Vpu inhibitor, and a viral Vif inhibitor.

Further examples of antiviral compounds include, but are not limited to, amantadine, rimantadine, zanamavir and oseltamavir (Tamiflu) for the treatment of flu and its associated symptoms. Antiviral compounds useful in the treatment of HIV include Combivir® (lamivudine-zidovudine), Crixivan® (indinavir), Emtriva® (emtricitabine), Epivir® (lamivudine), Fortovase® (saquinavir-sg), Hivid® (zalcitabine), Invirase® (saquinavir-hg), Kaletra® (lopinavir-ritonavir), Lexiva™ (fosamprenavir), Norvir® (ritonavir), Retrovir® (zidovudine) Sustiva® (efavirenz), Videx EC® (didanosine), Videx® (didanosine), Viracept® (nelfinavir) Viramune® (nevirapine), Zerit® (stavudine), Ziagen® (abacavir), Fuzeon® (enfuvirtide) Rescriptor® (delavirdine), Reyataz® (atazanavir), Trizivir® (abacavir-lamivudine-zidovudine) Viread® (tenofovir disoproxil fumarate) and Agenerase® (amprenavir). Other antiviral compounds useful in the treatment of Ebola and other filoviruses include ribavirin and cyanovirin-N (CV-N). For the treatment of herpes virus, Zovirax® (acyclovir) is available.

Examples of viral infections include but are not limited to, infections caused by all RNA viruses (including negative stranded RNA viruses, positive stranded RNA viruses, double stranded RNA viruses and retroviruses) and DNA viruses. Examples of viruses include, but are not limited to, HIV (including HIV-1 and HIV-2), parvovirus, papillomaviruses, measles, filovirus (for example, Ebola, Marburg), SARS (severe acute respiratory syndrome) virus, hantaviruses, influenza viruses (e.g., influenza A, B and C viruses), hepatitis viruses A to G, caliciviruses, astroviruses, rotaviruses, reovirus, coronaviruses, (for example, human respiratory coronavirus and SARS coronavirus (SARS-CoV), picornaviruses, (for example, human rhinovirus and enterovirus), Ebola virus, human herpesvirus (such as, HSV-1-9, including zoster, Epstein-Barr, and human cytomegalovirus), foot and mouth disease virus, human adenovirus, adeno-associated virus, respiratory syncytial virus (RSV), smallpox virus (variola), cowpox, monkey pox, vaccinia, polio, viral meningitis and hantaviruses.

For animals, viruses include, but are not limited to, the animal counterpart to any above listed human virus, avian influenza (for example, strains H5N1, H5N2, H7N1, H7N7 and H9N2), and animal retroviruses, such as simian immunodeficiency virus, avian immunodeficiency virus, pseudocowpox, bovine immunodeficiency virus, feline immunodeficiency virus, equine infectious anemia virus, caprine arthritis encephalitis virus and visna virus.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Results

In this study, modified mirror-image phage display screens and structure-based design were employed to discover shorter and more potent D-peptide Pocket-specific Inhibitors of Entry (PIE). The crystal structure of one of these inhibitors was determined in complex with a pocket mimic to understand the basis of how increased potency was achieved. Guided by this structure, a dramatically improved dimeric inhibitor was designed that is much more potent than any previously reported pocket-specific HIV-1 entry inhibitor. This combination of avidity and improved monomeric binding has now produced D-peptides that can be used in the treatment and prevention of HIV-1 infection.

Previously, Eckert et al. used mirror image phage display to discover a family of D-peptide HIV-1 entry inhibitors ($IC_{50}$=11-270 μM against HXB2 strain) that are specific for the hydrophobic pocket of the gp41 N-trimer. The phage library contained 10 randomized residues (10-mer) flanked by cysteines, which circularize the peptides and are essential for their inhibitory activity. However, due to the vast possible sequence diversity of this library, only one in ~3×10$^6$ sequences was screened, and it was therefore reasoned that more potent inhibitors of this type likely remained to be discovered.

Importantly, a consensus sequence ($CX_5$EWXWLC, SEQ ID NO: 33) was identified from the original phage screen that allowed for the development of a constrained library in which the consensus sequence (underlined) was fixed, but the other six residues were randomized. This constraint allowed for the construction of a library that exhaustively represents all possible sequences. A family of D-peptides with significantly improved average potency over the original D-peptides was identified. Surprisingly, one of the most potent D-peptides identified (2K-PIE1) was an 8-mer ($CX_3$EWXWLC, SEQ ID NO: 34) with two of the randomized residues deleted. This phage clone (PIE1-φ) was not intentionally part of the library and likely arose from a very rare replication error. The selection of this sequence despite its very low prevalence in the initial library showed that the 8-mer family was a richer source of tight binders than the 10-mers.

(1) Crystal Structure of the 2K-PIE1/IQN17 Complex

Figure 2:
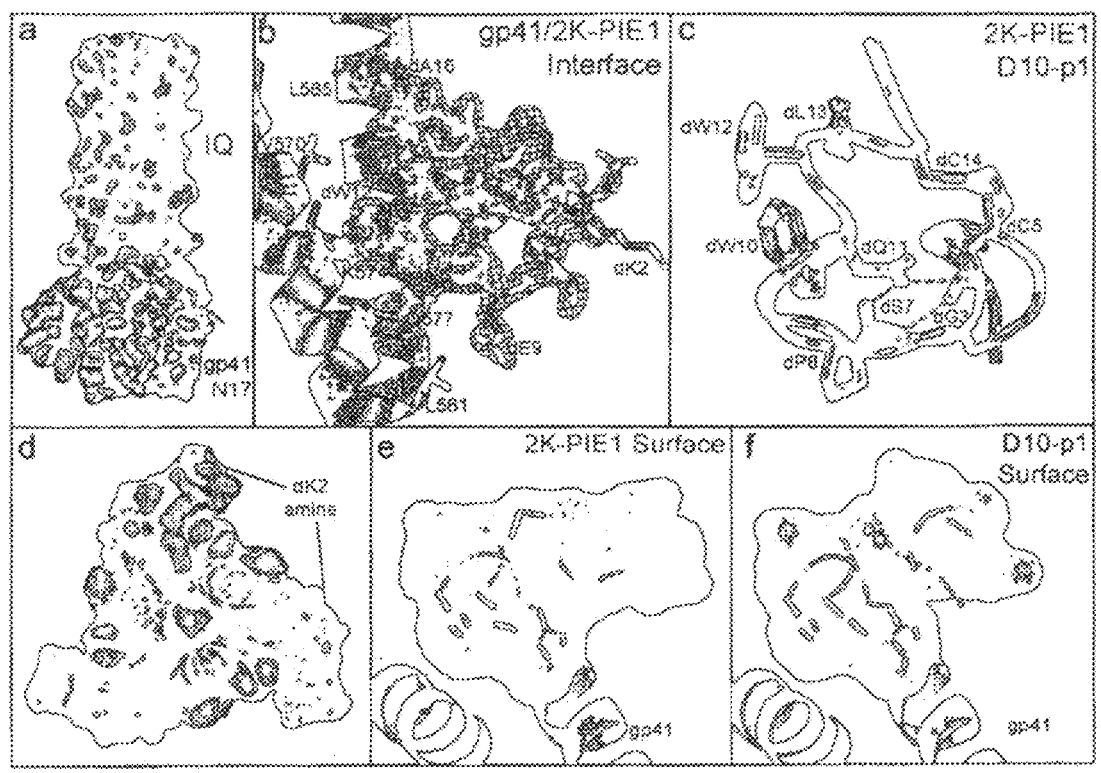
FIG. 2 shows structural analysis of the IQN17:2 K-PIE1 inhibitor complex. A) IQN17, consisting of IQ (orange) and gp41 (N17, gray) segments, with inhibitors (green, yellow, purple) located in the canonical gp41 binding pockets. The third inhibitor is mostly occluded in this view. B) Omit map for 2K-PIE1 contoured at 3.0 σ. Pocket residues (gray, HXB2 numbering) making hydrophobic contacts with 2K-PIE1 (green) are shown. Two hydrogen bonds (black) at the binding interface are also shown. C) Overlay of D10-p1 (slate) and 2K-PIE1 (green) superposed using the conserved residues dW10, dW12, and dL13 (all atoms, 2K-PIE1 numbering). Notable intramolecular hydrogen bonds unique to 2K-PIE1 are highlighted (dotted yellow lines). Intramolecular disulfide bonds (solid yellow) are also shown. D) End-on view of the complex (same color scheme as A) in which the surface from the last three residues of IQN17 have been removed. This view illustrates the packing of the inhibitor into the deep hydrophobic pocket. dK2 residues (blue), equivalent to the N-terminal Lys in PIE7 used for crosslinking, are highlighted. E) A slab view through the center of 2K-PIE1 (green) reveals an intact hydrophobic core (black) which excludes water. F) A similar view of D10-p5 (slate) reveals the presence of several water molecules in its core (black), which nearly form a water channel.
Figure 6:
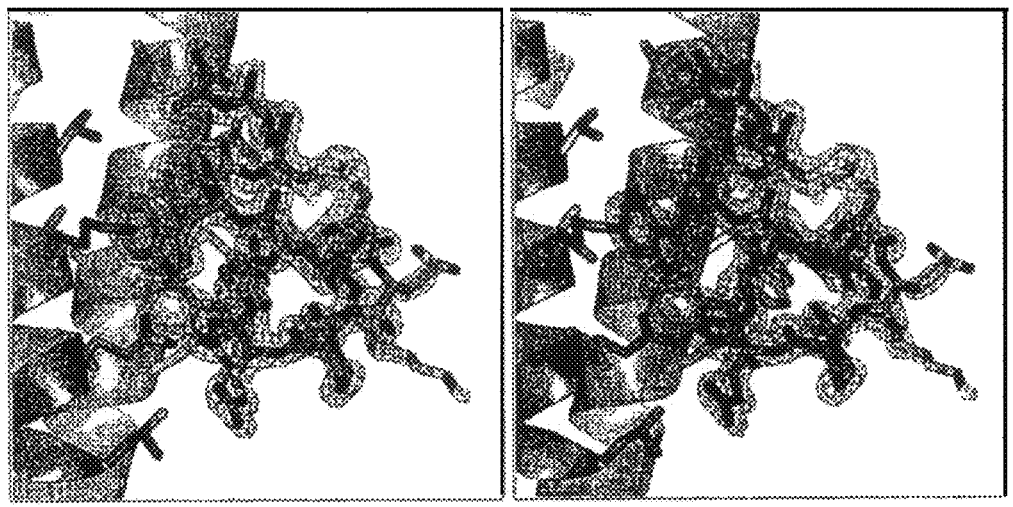
FIG. 6 shows wall-eyed stereoview of an electron density map of 2K-PIE1. View is the same as in FIG. 2B.

To more fully understand the interaction of 2K-PIE1 with its target, the co-crystal structure of 2K-PIE1 bound to the gp41 N-trimer pocket mimic IQN17 was solved (FIG. 2). The structure was solved at 1.7 Å by molecular replacement and contains two IQN17 monomers and two 2K-PIE1 inhibitors in the asymmetric unit, with crystallographic 3-fold axis generating two independent trimeric complexes (see Table 1 for a description of data collection and refinement statistics). The two complexes are highly similar (rmsd of 0.2 Å between 55 pairs of Cα atoms) although the N-terminal region (residues 1-4 of molecule B) of one complex is very poorly ordered. IQN17 molecule A, however, is well-ordered throughout, including both the N-terminal acetyl and C-terminal amide capping groups, and this molecule was used for structural analysis. Both 2K-PIE1 molecules are ordered throughout, with the exception of residues 1 and 2, which are completely disordered in one molecule, while residue 2 is very poorly ordered in the other. Excellent electron density is apparent for a number of important features of the inhibitor, including the main pocket-binding residues (dTrp10, dTrp12, and dLeu13) and the disulfide bond between dCys5 and dCys14 (FIG. 2B, FIG. 6).

Comparison of the 2K-PIE1 and D10-p1 structures, both in complex with IQN17, reveal a striking similarity in the pocket-binding interface (FIG. 2C). The IQN17 portion of each structure overlays with an rmsd of 0.3 Å between 45 pairs of Cα atoms, and the pocket is essentially unchanged. Comparing D-peptide inhibitors (2K-PIE1 numbering), the pocket-binding residues dTrp10, dTrp12, and dLeu13, as well as a small segment of helix at the C-terminus superimpose extremely well (FIG. 2C). Interestingly, dLeu13 has a different rotomer conformation in 2K-PIE1, in which the sidechain is flipped by 180°. These three residues contribute most of the gp41 binding surface for the inhibitor. Importantly, the amount of solvent accessible surface area buried by D10-p1 and 2K-PIE1 is also similar (504 Å$^2$ and 490 Å$^2$, respectively).

One major difference between the inhibitors is the path of the backbone on the distal side of the peptide (away from the pocket interface) (FIG. 2C). dPro8 in 2K-PIE1 appears to facilitate the turn required for circularization, possibly allowing other residues to adopt more relaxed confirmations. In support of this idea, a Pro in this position appears to be a better solution for 8-mers than other residues (see below). The more compact structure of 2K-PIE1 vs. D10-p1 (volume is 1743.5 vs. 1985.4 Å$^3$) allows it to form a better packed hydrophobic core (FIGS. 2E and 2F) that excludes the water molecules seen in the core of D10-p1 (FIG. 2F). The 2K-PIE1 inhibitor also contains a network of polar contacts not seen in the D10-p1 inhibitor. Notably, the dGln11 epsilon nitrogen makes hydrogen bonds with both the dSer7 and dCys5 main-chain carbonyls, thus helping to pack this tighter loop architecture (FIG. 2C). Also, a hydrogen bond between the dSer7 hydroxyl group and the dGly3 carbonyl allows 2K-PIE1 to pack its N-terminal region closer to the core of the inhibitor. In total, there are five new polar contacts (2.7-3.2 Å) unique to 2K-PIE1, while three such contacts are lost compared to D10-p1. Furthermore, the main-chain carbonyl of dGlu9 in the 2K-PIE1 structure is better positioned to participate in a hydrogen bond with Gln577 (HXB2 numbering) (FIG. 2B) than in the D10-p1 complex. These subtle changes at the binding interface, as well as the improved packing of 2K-PIE1, can contribute to its improved binding affinity. Overall, the comparison shows that the reduction in size (10-mer to 8-mer) creates a better packed and more compact D-peptide without compromising the binding interface.

(2) Phage Display of an 8-mer Library

The surprising emergence of 2K-PIE1 from a 10-mer library and its apparent structural advantages led to the performance of a comprehensive phage display study of 8-mers. An 8-mer phage library of the form $CX_4WXWLC$ (SEQ ID NO: 35) was generated, which contained $1.5 \times 10^8$ clones and exhaustively covers $3.4 \times 10^7$ possible sequences. This library was initially screened using solution-phase phage display (Barbas 2001). In this panning strategy, the phage and target were allowed to bind in solution, followed by a rapid precipitation of the target and bound phage using magnetic beads. This method reduces the intermolecular avidity effect seen in traditional phage display when one phage binds to multiple immobilized targets. In solution-phase phage display, selection pressure is increased by dropping the concentration of target in solution during the binding phase.

The target was the $2^{nd}$ generation pocket mimic IZN17 (Eckert 2001), which is more soluble and stable than IQN17. Four rounds of solution-phase phage display were performed in which the target concentration was lowered from 100-0.1 nM. Good progress was made during early rounds, with the library as a whole binding as well as PIE1-φ following round two. However, even in the absence of intermolecular avidity, the phage bound the target much better than expected based on the $K_D$'s of the D-peptides (Cole 2001). Because the target is a trimer, the polyvalently displayed library peptides can simultaneously bind multiple binding sites within the same trimer resulting in an intramolecular avidity effect. An emerging consensus sequence in about half of the phage clones (CDYXEWXWLC, SEQ ID NO: 36) was identified. Several of these phage clones were directly compared in a clonal phage binding assay, and one of them, PIE2-φ, bound ~5-fold better than PIE1-φ.

In order to increase selection pressure without causing dissociation of IZN17, an L-amino acid version of 2K-PIE2 was used as a soluble competitor during solution-phase binding. For these experiments, IZN17 was fixed at 10 nM and the concentration of L-2K-PIE2 competitor was ramped from 0 to 35 μM over several rounds of phage display. By round five, several interesting sequences appeared (PIE7-10-φ, FIG. 3). One of these (PIE10-φ) is a mutant phage that started to dominate the library. Round six was nearly completely dominated by PIE10-φ and another mutant clone PIE11-φ. Both have mutations in their C-terminal flanking residues, which link the library peptide to the phage g3 protein. As with the discovery of 2K-PIE1, these mutant clones were not intentionally part of the library and were originally extremely underrepresented.

Figure 3:
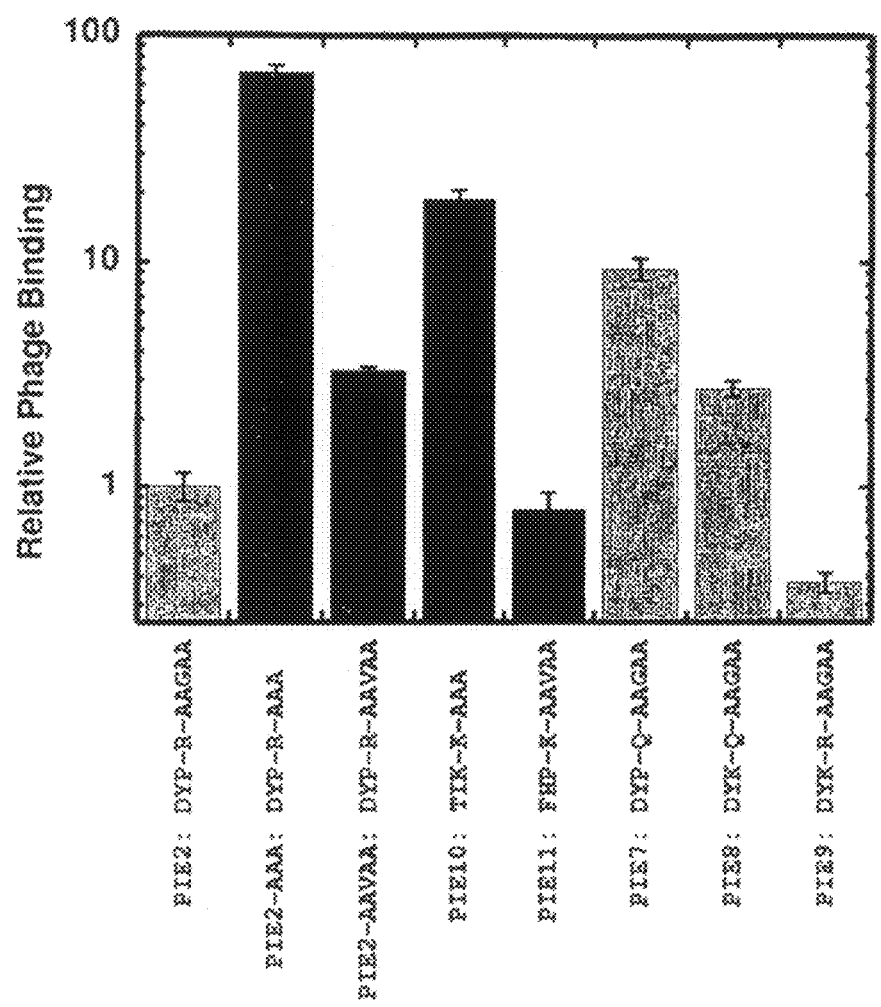
FIG. 3 shows a phage clone binding assay. The binding of clonal phage to IZN17, normalized to PIE2-ϕ. Error bars represent the s.e.m. from parallel duplicate experiments done twice on separate days (n=4). The name and variable sequence (DGACX$_3$EW-X-WLC-X$_{3-5}$) of each clone are listed below each bar. Black bars represent mutant C-terminal flanking sequences found in the library. Dark gray bars represent cloned controls containing the PIE2-ϕ sequence with mutant C-terminal flanking sequences. Light gray bars represent wild type sequences found in the library.

A clonal phage binding assay was performed on each of the selected sequences to assess whether these mutations really contributed to IZN17 binding. FIG. 3 indicates that PIE10-φ binds IZN17 ~18-fold better than PIE2-φ and that PIE11-φ is similar to PIE2-φ, despite a core sequence that appears unfavorable for pocket binding. In order to directly compare the mutant flanking sequences to wild type, both mutant C-terminal flanking sequences were cloned onto PIE2-φ (PIE2-AAA-φ, PIE2-AAVAA-φ). Both mutants improved binding compared to wt PIE2-φ, with the AAA sequence conferring a dramatic ~70-fold advantage.

Of the remaining phage clones tested in the binding assay, PIE7-φ and PIE8-φ bind IZN17 ~10- and ~2-fold better than PIE2-φ, respectively, and PIE2-φ binds ~3-fold better than PIE9-φ. Finally, several pairwise comparisons can be made from the data in FIG. 3, which highlight the importance of optimizing individual residues even if they are not directly involved in binding the hydrophobic pocket. For example, the only difference between the sequence of PIE2 and PIE7 is the identity of residue 10, in which Gln is significantly better than Arg. Similarly, PIE8 only differs from PIE7 at residue seven where Pro is preferred.

(3) Potency of D-Peptides Against HXB2 Viral Entry

Figure 4:
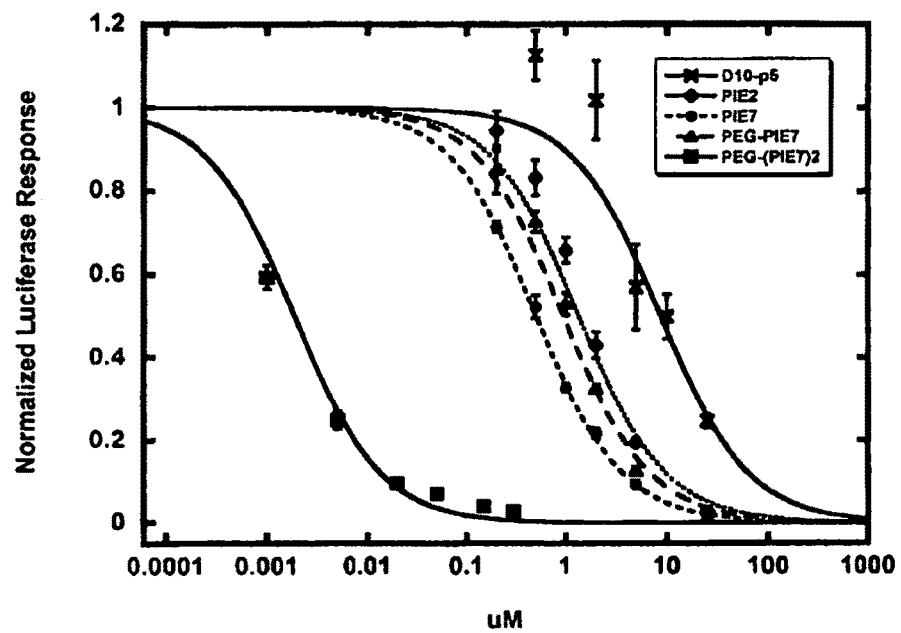
FIG. 4 shows representative HXB2 viral entry inhibition data. Each point represents the average of quadruplicate measurements normalized to uninhibited control. Error bars represent the s.e.m.

D-peptide versions of the best phage clones were synthesized and tested in a standard single-cycle viral infectivity assay (Table 3, FIG. 4). As expected from the phage binding data, peptides corresponding to the non-cheater sequences (PIE2, 7, and 8) inhibit viral entry with $IC_{50}$'s of 1.32, 0.62, and 1.68 μM, respectively. The best of these $2^{nd}$ generation D-peptides (PIE7) is ~15-fold more potent that the best previously reported $1^{st}$ generation D-peptide (D10-p5), which is included for comparison. Note that the relatively small difference between the $IC_{50}$ of PIE2 and PIE7 is magnified in the phage binding assay. This effect is likely the result of intramolecular avidity and can be necessary to select the best clones in a minimal number of rounds of phage display before other unwanted biases become prevalent.

To evaluate if the C-terminal mutation in PIE10-φ affects inhibitory potency, PIE2 was synthesized with an Ala-Ala-Ala C-terminal flanking sequence. The inhibitory potency of PIE2-AAA was nearly indistinguishable from the potency of PIE2 (Ala-Ala C-terminus) (Table 3). This result shows that this mutation is likely to improve phage binding by a cheater mechanism, and peptides containing this sequence were not pursued further.

It was noted by Eckert et al. (Eckert 1999) that introduction of Lys residues at the N-terminus of D-peptides, required for solubility, made them less potent inhibitors. 2K-PIE2 is ~2-fold less potent than PIE2 (Table 3). Since 1K-versions of the $2^{nd}$ generation D-peptides have good solubility and improved potency, it was decided to make 1K—the standard N-terminus of the $2^{nd}$ generation D-peptides (all $2^{nd}$ generation peptides have a single N-terminal Lys unless otherwise labeled, e.g., PIE2 vs. 2K-PIE2).

(4) Dimeric D-Peptides

Based on the 2K-PIE1 crystal structure and the observation of intramolecular avidity in phage display, it was predicted that dimeric D-peptides would have significantly improved affinity for the N-trimer and enhanced antiviral potency. To test this idea, a bis(NHS-ester)PEG crosslinker was used to dimerize PIE2-AAA and PIE7 via their unique primary amines (N-terminal Lys) (FIG. 2D). PEG is an ideal material for crosslinking as it is highly flexible, very soluble, non-immunogenic, and has been used in several approved therapeutic peptides and proteins (Harris 2003). The length of PEG spacer (35 Å) was chosen to cover, with some additional slack, the distance between the N-termini of neighboring D-peptides in the crystal structure. The resulting dimeric inhibitors, PEG-(PIE2-AAA)$_2$ and PEG-(PIE7)$_2$, have IC$_{50}$'s of 21 nM and 1.9 nM (Table 3, FIG. 4), respectively. These values represent a dramatic ~70- and 325-fold improvement over the corresponding monomers. These data also indicate that modest improvements in the potency of monomeric inhibitors are magnified by avidity in the dimer, as also observed in the phage display. The potency of PEG-(PIE7)$_2$ is comparable to Fuzeon (Table 3).

To control for possible non-specific effects of the PEG moiety, mono(NHS-ester)PEG was reacted with PIE7 to generate PEG-PIE7. PEG-PIE7 shows a ~1.5-fold reduction in potency compared to the unmodified PIE7. Therefore, the improved potency of the dimers cannot be attributed to an interaction of the PEG with virus, cells, or the D-peptide, but is a genuine avidity effect caused by two D-peptides binding to the N-trimer. As a final control, the crosslinking reagent itself (quenched by reaction with Tris) is non-toxic up to 100 µM in this assay.

(5) Surface Plasmon Resonance Characterization of D-Peptide Inhibitors

To determine if the improved potency of these inhibitors stems from optimization of affinity for the pocket, the binding properties of the D-peptides to an immobilized N-trimer mimic (IZN36) was characterized using surface plasmon resonance (SPR) (Table 3). The measured K$_D$ values are in good correlation with antiviral IC$_{50}$'s, indicating that D-peptide binding to a pocket mimic in vitro is a good predictor of antiviral potency.

Figure 5:
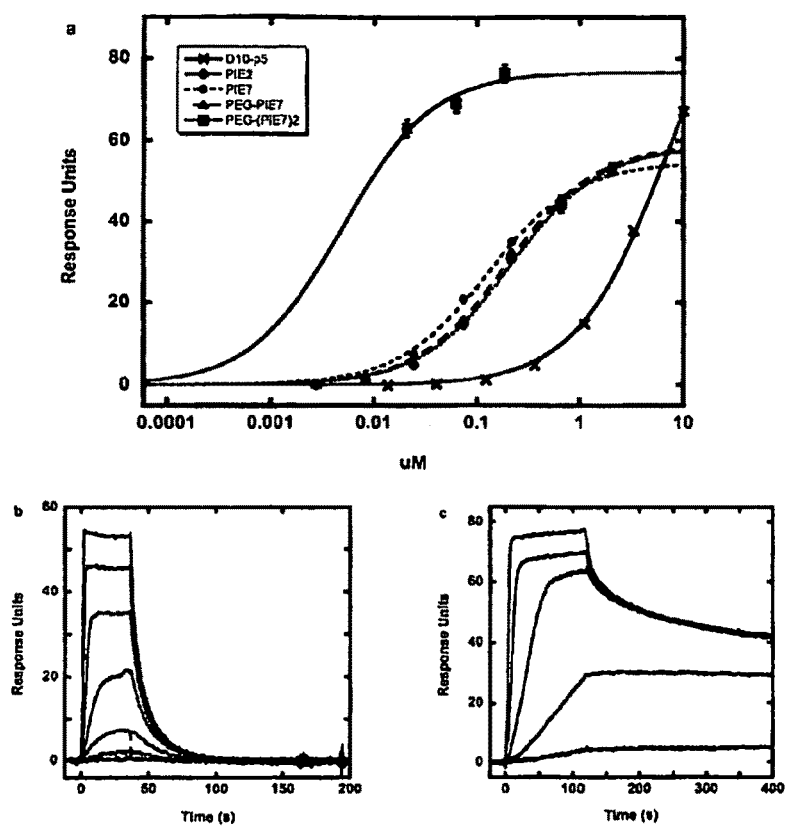
FIG. 5 shows biosensor analysis. A) Binding isotherms of selected inhibitors at 20° C. with immobilized IZN36 target (labels are same as FIG. 4). Each point represents the average of at least two measurements. Error bars represent the s.e.m. PEG-(PIE7)$_2$ did not reach equilibrium at low concentration points, so these points are masked. B-C) Sensorgrams of a 3-fold concentration series for PIE7 and PEG-(PIE7)$_2$, respectively. This comparison of the PIE7 monomer and dimer reveals the dramatically slowed, mass transport-limited, dissociation of the dimer.

An overlay of the binding isotherms of each inhibitor (FIG. 5A) reveals the reduction in K$_D$ between the best 1$^{st}$ (D10-p5) and 2$^{nd}$ (PIE7) generation monomers, as well as the dramatic improvement that the dimer enjoys over its monomer. Both the PIE7 monomer and dimer have similar rapid association rates and the improved K$_D$ of the dimer can be mainly driven by a slowed dissociation rate (FIG. 5B-C). Thus, these inhibitors do not appear to be limited by association rate as is the case with some entry inhibitors (Steger 2006).

(6) D-Peptide Inhibitors are Also Active Against the Primary Strain JRFL

Figure 7:
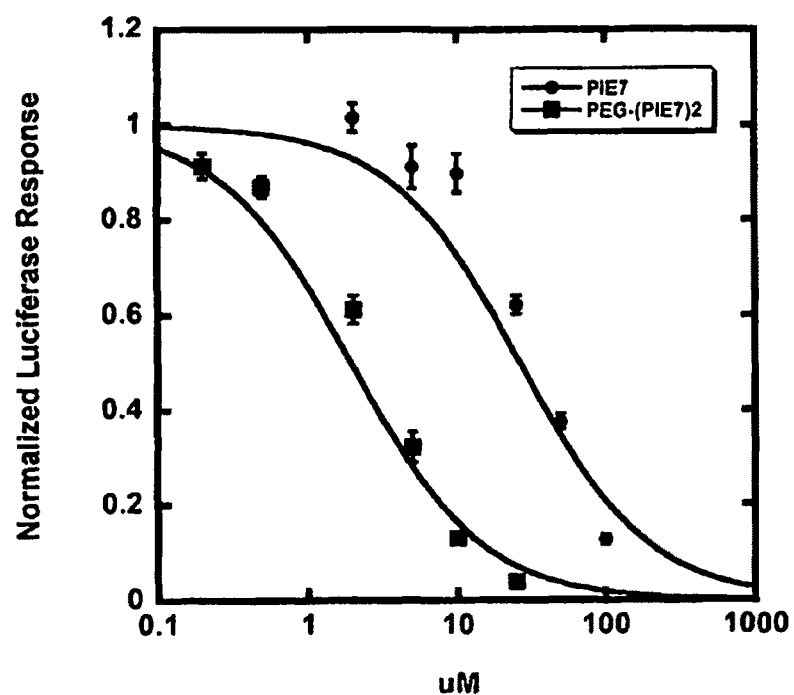
FIG. 7 shows representative JRFL viral entry inhibition data. Each point represents the average of quadruplicate measurements normalized to uninhibited control. Error bars represent the s.e.m.

While HXB2 is a commonly used lab-adapted HIV-1 isolate, it is often more vulnerable to inhibition than primary clinical HIV-1 isolates. Initial testing against the CCR5-tropic primary HIV-1 isolate, JRFL, indicates that PIE7 and PEG-(PIE7)$_2$ inhibit with IC$_{50}$'s of 24.4 and 2.3 µM, respectively (FIG. 7). This ~40-fold reduction in potency of PIE7 against JRFL is within the range seen with many other entry inhibitors (Miller 2005; Bianchi 2005). This phenomenon has been correlated with the faster fusion kinetics of JRFL, particularly with the target cell lines used in standard viral entry assays, which overexpress CCR5 at levels much higher than HIV-1's natural target cells (e.g., macrophages) (Platt 2005; Choudhry 2006). The CCR5 co-receptor inhibitor, TAK779, was used to effectively lower the amount of available coreceptor on the surface of the target cells. Addition of 100 nM TAK779 (IC$_{90}$) improved the potency of PIE7 more than 3-fold, indicating that PIE7's potency is likely limited by high coreceptor levels and that its inhibition is synergistic with TAK779.

b) Discussion

The development of potent HIV-1 entry inhibitors demonstrates that D-peptides can form high affinity interactions with natural proteins and be used as therapeutic agents. Furthermore, it was shown that a "bootstrapping" approach using the best currently available soluble competitors can be used to apply selection pressure and identify progressively tighter binders.

(1) Uses of D-peptides

The success of Fuzeon in the clinic demonstrates that inhibition of viral entry is an effective means of controlling HIV-1, but its utility is limited by serious practical problems. Here, the discovery of potent D-peptide inhibitors is reported, including a dimer with similar potency to Fuzeon against HXB2. These D-peptides have significant theoretical advantages over the L-peptide Fuzeon. Since D-peptides are not degraded by proteases they have the potential for: oral bioavailability, extended persistence in circulation, reduced immunogenecity (Chong 1996), long shelf life, and use in harsh mucosal environments as a topical prophylactic microbicide. The D-peptides disclosed herein target the highly conserved gp41 hydrophobic pocket region and have better resistance profiles than Fuzeon (Rimsky 1998), which targets a less well conserved region of gp41. Since the hydrophobic pocket is not targeted by Fuzeon or other entry inhibitors currently in advanced clinical trials (e.g., BMS-378806, PRO542, Vicriviroc, Maraviroc), the D-peptides disclosed herein can be synergistic with these inhibitors and could form part of a powerful entry inhibitor "cocktail", similar to the mixtures of HIV-1 protease and reverse transcriptase inhibitors currently used in HAART (highly active anti-retroviral therapy). Indeed, PIE7's inhibitory activity is at least additive with Fuzeon against viral entry. Finally, the smaller size (and therefore easier synthesis) of D-peptides dramatically decreases the complexity and cost of their large-scale production and purification.

c) Materials and Methods (1) Peptide Synthesis and Purification

All synthesized peptides were capped with N-terminal acetyl and C-terminal amide groups, and their masses confirmed by MALDI-TOF. Crude peptides were purified by reverse-phase HPLC (RP-HPLC) on a C18 column (Vydac) and lyophilized. D-peptide inhibitors were oxidized at (mg/mL) overnight at 37° C. in 50 mM Tris, pH 8.0, 2% DMSO, and repurified using RP-HPLC.

PEG-(PIE7)$_2$ was made by incubating PIE7 (~2 mM) with freshly prepared crosslinker (Bis-dPEG$_9$™ NHS ester, Quanta BioDesign, #10246) at a 1:0.6 (peptide:PEG) molar ratio in 50 mM NaHPO$_4$, pH 7.0, for 2 h at RT. PEG-(PIE2-AAA)$_2$ was made using a similar protocol. PEG-PIE7 was made using a similar protocol with NHS-m-dPEG™ (Quanta BioDesign, #10260) at a 1:2 (peptide:PEG) molar ratio.

(2) Protein Expression and Purification

Cys-Gly-Gly-Asp-IZN36 (IZN36) was expressed in BL21 (DE3)pLysS cells (Stratagene) using a pET14b expression plasmid (Hamburger 2005). Inclusion bodies containing IZN36 were solubilized using 6M GuHCl and 250 mM beta-mercaptoethanol (BME), precipitated by dialyzing into 50 mM NaHPO$_4$, 100 mM NaCl, 1 mM BME, and re-solubilized using 6M GuHCl and 250 mM BME. This sample, >95% pure by SDS-PAGE, was further purified by RP-HPLC on a C4 column (Vydac). Lyophilized sample was re-dissolved in biotinylation reagent (0.5 mM biotin-HPDP (Pierce), 10% DMSO, PBS pH 7.4) and incubated at RT for 2.5 h. After thrombin (Novagen) cleavage to remove the His-tag (2.5 U/mg peptide, overnight incubation at 37° C.), the final product was purified by RP-HPLC (Vydac C4 column) and verified by MALDI-TOF.

(3) Crystallography

Lyophilized protein was resuspended in water to make a 10 mg/ml sample (total protein concentration) containing IQN17 and 2K-PIE1 at a ratio of 1:1.1. This solution was centrifuged (~200,000×g) for 30 min at 4° C. to remove insoluble aggregates prior to crystallization. Crystals grew in sitting drops (0.4 μl protein solution and 0.4 μl reservoir) at 21° C. against a reservoir of 25-27% PEG 2000 MME, 0.1 M sodium acetate pH 4.6, 0.2 M Ammonium sulfate, 0.2-0.4 M $YCl_3$. Crystals were flash frozen in liquid nitrogen directly from their mother liquor.

Data were collected at the NSLS beamline X26-C and processed with DENZO and SCALEPACK (Otwinowski 1997). The data exhibited partial merohedral twinning as judged by the method of Yeates (UCLA twinning server, http://nihserver.mbi.ucla.edu/Twinning/) with a twin fraction estimate of 30.3%.

The structure was solved by molecular replacement using PHASER (McCoy 2005) implemented in the CCP4 suite (CCP4 1994). The search model was generated from the structure of the IQN17/D10-p1 peptide complex (Eckert 1999) with surface exposed side chains truncated at the C-β position. The model was refined using the twinning routines for simulated annealing followed by rounds of positional refinement, minimization, and B-factor refinement within CNS (Brunger 1998). Model building was performed using COOT (Emsley 2004). All residues fall within the favorable or most favorable sections of the Ramachandran plot (PROCHECK in CCP4).

(4) Phage Display

An M13KE plasmid (NEB) was modified by inserting an ampicillin resistance cassette into the Acc65 I and Eag I sites. A library oligonucleotide (5'-catgtttcggccgcgcccgccgcgca-cagccamnnccamnmnnmnnmnnacacgcgccatcagaatgag-3', SEQ ID NO: 37) and extension primer (5'-aaaaaaaaaaaaaaaaaaaaggtacctttctattctcattctgatggcgcgtgt-3', SEQ ID NO: 38) were made and cloning proceeded essentially as described by Noren and Noren, 2001 (Noren 2001). A polyvalent g3 fusion library containing 1.5×10⁸ primary clones was made to cover a theoretical diversity of 3.4×10⁷ by electroporation (MicroPulser, Biorad) of ~0.9 μg of purified library DNA mixed with 480 μL of electrocompetent SS320 cells (Sidhu 2000).

For the first four rounds of solution-phase phage display, the D-IZN17 concentration was 100, 1, 0.1 and 0.1 nM at 37° C. In the traditional solution-phase phage display protocol, $10^{10}$ phage were incubated at RT in 25 μL of freshly prepared TTBS (50 mM Tris pH 7.4, 150 mM NaCl, 0.1% Tween-20) containing 10% Superblock (Pierce) for 2 h. 25 μL of T1 streptavidin-coated magnetic beads (Dynal) were blocked in Superblock for 1 h at 4° C. and briefly rinsed in TTBS prior to addition to the phage/target mix. After incubation for 1 min, the beads were magnetically pelleted and immediately washed 6 times with 500 μL TTBS. 100 μM D-biotin was included in the buffer during the 1ˢᵗ wash to block excess streptavidin sites. The beads were then incubated with 50 μL of elution buffer (0.2 M glycine, pH 2.2) for 10 min. After pelleting, the supernatant was collected and neutralized with 7.5 μL of 1 M Tris, pH 9.1. Eluted phage were titered and amplified using XL-1 Blue cells (Stratagene) essentially as described in the NEB PhD System instruction manual. Amplified phage were flash-frozen in liquid nitrogen and stored at −80° C. Under these storage conditions, titers were maintained for >6 months.

For the solution-phase phage display with soluble competitor, amplified output from the above round 1 was used. For rounds 2 to 6, d 10 nM D-IZN17 was used, and added increasing concentrations of soluble competitor (L-2K-PIE2, from 0 μM in round 2 to 35 μM in round 6). Otherwise, the phage display was performed as described above. Phage binding assays were performed in the presence of 25 μM L-2K-PIE2 using the protocol described above. DNA sequencing of phage clones was performed using DNA from colony PCR treated with ExoSAP-It (USB).

(5) Viral Infectivity Assay:

All studies were done using the HXB2 strain unless otherwise specified. Viral infectivity was measured essentially as previously described (Hamburger 2005) with several modifications. 8 μg/mL DEAE-Dextran was used as a fusion enhancer in all assays. Media was changed 22-26 h following infection. $IC_{50}$ values were calculated by fitting normalized data to the following equation: $y=1/(1+[inhibitor]/IC_{50})$. Fits were weighted by the absolute s.e.m. from quadruplicate points with the minimum allowable error set to 1%. Samples requiring DMSO for solubility (D10-p5, PEG-$(PIE2-AAA)_2$, PEG-$(PIE7)_2$, and PEG-PIE7) were tested at 1% final DMSO concentration and normalized to an uninhibited control containing 1% DMSO. The following reagents were obtained through the AIDS Research and Reference Reagent Program, Division of AIDS, NIAID, NIH: TAK779 and T-20 (Fuzeon) from NIAID and Roche, respectively.

(6) Surface Plasmon Resonance Analysis:

SPR was performed essentially as described (Hamburger 2005). Briefly, biotinylated IZN36 was captured onto a SA (Pierce) surface, and a free SA surface served as the reference control. Each binding study was performed in duplicate at 20° C. using a 3-fold decreasing concentration series starting from 10 μM for D10-p5, 189 nM for PEG-$(PIE)_2$, or 2 μM (all others). Only 2K-PIE1 and PEG-$(PIE)_2$ required a specific regeneration step (one 20 s pulse of 6M GuHCl). The IZN36 surface was very stable to this regeneration condition. Data were analyzed using Scrubber2 (Biologic Software).

TABLE #2

Data collection and refinement statistics

| | IQN17:2K-PIE1 complex |
|---|---|
| Data collection | |
| Space group | $P6_3$ |
| Cell dimensions | |
| a, b, c (Å) | 46.84, 46.84, 137.08 |
| Resolution (Å) | 50-1.73 |
| $R_{sym}$ (%) | 9.4 (48.1) |
| I/σ(I) | 17.6 (2.2) |
| Completeness (%) | 95.3 (77.5) |
| Redundancy | 5.6 (3.4) |
| Refinement | |
| Resolution (Å) | 50-1.73 |
| No. reflections | 612,619 |
| Unique reflections | 33,506 |
| $R_{work}/R_{free}$ (%) | 19.3/23.0 |
| twinning fraction | 0.326 |
| No. atoms | |
| Protein | 737 |
| Ligand/ion | 227/6 |
| Water | 216 |
| B-factors (Å)² | |
| Protein | 28.2 |
| Ligand/ion | 28.6/28.0 |
| Water | 38.6 |
| R.m.s deviations | |
| Bond lengths (Å) | 0.011 |
| Bond angles (°) | 1.414 |

Highest resolution shell (1.79-1.73 Å) is shown in parentheses.

TABLE #3

D-peptide binding and neutralization

| Sample | Sequence | IC$_{50}$ (μM)† (HXB2) | K$_D$ (μM)† |
|---|---|---|---|
| D10-p5 | KKGACELLGWEWAWLCAA, SEQ ID NO: 1 | 9.51* | 6.8 |
| 2K-PIE1 | KKGACESPEWRWLCAA, SEQ ID NO: 2 | 2.22 | ND |
| 2K-PIE2 | KKGACDYPEWRWLCAA, SEQ ID NO: 3 | 2.57 | 0.26 |
| PIE2-AAA | KGACDYPEWRWLCAAA, SEQ ID NO: 4 | 1.44 | — |
| PIE2 | KGACDYPEWRWLCAA, SEQ ID NO: 5 | 1.32 | 0.20 |
| PIE7 | KGACDYPEWQWLCAA, SEQ ID NO: 6 | 0.62 | 0.12 |
| PIE8 | KGACDYKEWQWLCAA, SEQ ID NO: 7 | 1.68 | 0.19 |
| PEG-PIE7 | PEG-KGACDYPEWQWLCAA, SEQ ID NO: 8 | 0.94 | 0.19 |
| PEG-(PIE7)$_2$ | PEG-(KGACDYPEWQWLCAA)$_2$, SEQ ID NO: 9 | 0.0019 | ~0.001 |
| Fuzeon | — | 0.0037 | — |

†IC$_{50}$ s.e.m. is <25% and K$_D$ s.e.m. is <5% for duplicate assays for all values.
*Toxicity was observed at 100 μM for D10-p5 and this point was excluded. No other toxicity was observed.
ND = Not determined due to complex binding behavior.

2. Example 2

Further Inhibitory D-Peptides

Disclosed herein are D-peptides that are Pocket-specific Inhibitors of Entry (PIE). Examples include: PIE7-GK (GACDYPEWQWLCAAGK, SEQ ID NO: 23). This peptide is the same as PIE7, except that the Lys has been moved to the C-terminus. The move results in slightly enhanced potency and allows for the crosslinking of peptides via their C-termini.

PIE7-GKK (GACDYPEWQWLCAAGKK, SEQ ID NO: 24). This is a double Lys variant of PIE7-GK, and serves as a central peptide in trimeric PIE7 (the central PIE7-GKK is connected to two flanking PIE7-GK peptides). These connections are all via the C-terminus.

K-PIE7-GK (KGACDYPEWQWLCAAGK, SEQ ID NO: 25). This double Lys variant of PIE7-GK serves as a central peptide in trimeric PIE7 (the central K-PIE7-GK is connected to two flanking peptides—PIE7-GK and PIE7). These connections link the N- to C-termini of neighboring peptides.

PIE7-GK-PEG4: (PIE7-GK with PEG4 attached). This peptide is a control to determine how well PEG additions are tolerated on the C-terminus of the D-peptides. From this peptide, it was learned that such additions are well tolerated.

This group of new peptides arose from optimization of the flanking sequences:

```
PIE12:    HPCDYPEWQWLCELGK    (SEQ ID NO: 26)

PIE13:    HPCDYPEWQWLCKLGK    (SEQ ID NO: 27)

PIE14:    HPCDYPEWQWLCRLGK    (SEQ ID NO: 28)

PIE15:    HACDYPEWQWLCELGK    (SEQ ID NO: 29)
```

Table 4 (below) discloses the inhibitory data for the peptides above, as well as other D-peptides previously discussed and other inhibitors (C37 and Fuzeon).

TABLE 4

Inhibitory Potency of D-peptides against HXB2 and JRFL Pseudovirion Entry

| Sample | IC$_{50}$ (nM)† (HXB2) | IC$_{50}$ (nM) (JRFL) |
|---|---|---|
| PIE7 | 620 | 24000 |
| PIE7-GK | 389 | 15800 |
| PIE7-GKK | 382 | 19100 |
| K-PIE7-GK | ND | 14800 |
| PIE7-GK-PEG$_4$ | 351 | 13100 |
| PIE12 | 37.1 | 578 |
| PIE13 | 41.3 | 1470 |
| PIE14 | 33.1 | 1050 |
| PIE15 | 66.7 | 1450 |
| N$_9$N(PIE7)$_2$ | 1.9 | 2300 |
| N$_9$C(PIE7)$_2$ | 0.329 | 313 |
| C$_9$C(PIE7-GK)$_2$ | 0.354 | 215 |
| N$_5$N(PIE7)$_2$ | 1.13 | 1410 |
| N$_5$C(PIE7)$_2$ | 0.575 | 300 |
| C$_5$C(PIE7-GK)$_2$ | 0.355 | 203 |
| N$_0$N(PIE7)$_2$ | 0.801 | 1090 |
| N$_0$C(PIE7)$_2$ | 0.534 | 402 |
| C$_5$C(PIE12)$_2$ | 0.292 | 14.2 |
| PEG$_5$-(PIE13)$_2$ | ND | 15.1 |
| N$_9$N(PIE7)$_3$ | 0.25 | 220 |
| C$_5$C(PIE7-GK)$_3$ | 0.130 | 6.73 |
| C$_5$C(PIE12)$_3$ | ND | 2.77 |
| C$_0$C(PIE7-GK)$_3$ | 0.117 | 16.1 |
| PIE7-GK long claw | 0.124 | 20.6 |
| PIE7-GK short claw | 0.234 | 86.6 |
| C37 | 1.4 | 13.0 |
| Fuzeon | 3.7 | 5.0 |

†IC$_{50}$ s.e.m. is <20% and K$_D$ s.e.m. is <5% for duplicate assays for all values
ND = Not determined.

G. SEQUENCES

```
                                            (SEQ ID NO: 1)
KKGACELLGWEWAWLCAA (SEQ ID NO: 2)
KKGACESPEWRWLCAA (SEQ ID NO: 3)
KKGACDYPEWRWLCAA (SEQ ID NO: 4)
KGACDYPEWRWLCAAA (SEQ ID NO: 5)
KGACDYPEWRWLCAA (SEQ ID NO: 6)
KGACDYPEWQWLCAA (SEQ ID NO: 7)
KGACDYKEWQWLCAA (SEQ ID NO: 8)
KGACDYPEWQWLCAA (SEQ ID NO: 9)
(KGACDYPEWQWLCAA)$_2$
```

G. SEQUENCES

| Sequence | |
|---|---|
| KKGACPREWHWLCAA | (SEQ ID NO: 10) |
| GACPREWHWLCAA | (SEQ ID NO: 11) |
| KKGACDYWEWRWLCAA | (SEQ ID NO: 12) |
| DGACDYPEWRWLCAA | (SEQ ID NO: 13) |
| KKGAGDDPDWQWLCAA | (SEQ ID NO: 14) |
| KKGACEDPDWQWLCAA | (SEQ ID NO: 15) |
| KKGACEDPEWQWLCAA | (SEQ ID NO: 16) |
| KKGACNDPEWQWLCAA | (SEQ ID NO: 17) |
| DGACESPEWQWLCAAGAA | (SEQ ID NO: 18) |
| ACPPEWHWLCGGGSA | (SEQ ID NO: 19) |
| ACPVEWRWLCGGGSA | (SEQ ID NO: 20) |
| ACPIEWRWLCGGGSA | (SEQ ID NO: 21) |
| ACPREWHWLCGGGSA | (SEQ ID NO: 22) |
| GACDYPEWQWLCAAGK | (SEQ ID NO: 23) |
| GACDYPEWQWLCAAGKK | (SEQ ID NO: 24) |
| KGACDYPEWQWLCAAGK | (SEQ ID NO: 25) |
| HPCDYPEWQWLCELGK | (SEQ ID NO: 26) |
| HPCDYPEWQWLCKLGK | (SEQ ID NO: 27) |
| HPCDYPEWQWLCRLGK | (SEQ ID NO: 28) |
| HACDYPEWQWLCELGK | (SEQ ID NO: 29) |
| EWXWL | (SEQ ID NO: 30) |
| WXWL | (SEQ ID NO: 31) |
| KKGAC | (SEQ ID NO: 32) |
| CX$_5$EWXWLC | (SEQ ID NO: 33) |
| CX$_3$EWXWLC | (SEQ ID NO: 34) |
| CX$_4$WXWLC | (SEQ ID NO: 35) |
| CDYXEWXWLC | (SEQ ID NO: 36) |
| catgtttcggccgcgcccgccgcgcacagccamnnccamnnmnnmnnmnn acacgcgccatcagaatgag | (SEQ ID NO: 37) |
| aaaaaaaaaaaaaaaaaaaaggtacctttctattctcattctgatggcgc gtgt | (SEQ ID NO: 38) |

H. REFERENCES

1. Lu, M., Blacklow, S. C. & Kim, P. S. A trimeric structural domain of the HIV-1 transmembrane glycoprotein. *Nat Struct Biol* 2, 1075-82 (1995).
2. Chan, D. C., Fass, D., Berger, J. M. & Kim, P. S. Core structure of gp41 from the HIV envelope glycoprotein. *Cell* 89, 263-73 (1997).
3. Weissenhorn, W., Dessen, A., Harrison, S. C., Skehel, J. J. & Wiley, D. C. Atomic structure of the ectodomain from HIV-1 gp41. *Nature* 387, 426-30 (1997).
4. Tan, K., Liu, J., Wang, J., Shen, S. & Lu, M. Atomic structure of a thermostable subdomain of HIV-1 gp41. *Proc Natl Acad Sci USA* 94, 12303-8 (1997).
5. Wild, C., Oas, T., McDanal, C., Bolognesi, D. & Matthews, T. A synthetic peptide inhibitor of human immunodeficiency virus replication: correlation between solution structure and viral inhibition. *Proc Natl Acad Sci USA* 89, 10537-41 (1992).
6. Jiang, S., Lin, K., Strick, N. & Neurath, A. R. HIV-1 inhibition by a peptide. *Nature* 365, 113 (1993).
7. Eckert, D. M. & Kim, P. S. Mechanisms of viral membrane fusion and its inhibition. *Annu Rev Biochem* 70, 777-810 (2001).
8. Chan, D. C. & Kim, P. S. HIV entry and its inhibition. *Cell* 93, 681-4 (1998).
9. Furuta, R. A., Wild, C. T., Weng, Y. & Weiss, C. D. Capture of an early fusion-active conformation of HIV-1 gp41. *Nat Struct Biol* 5, 276-9 (1998).
10. Root, M. J. & Steger, H. K. HIV-1 gp41 as a target for viral entry inhibition. *Curr Pharm Des* 10, 1805-25 (2004).
11. Eckert, D. M., Malashkevich, V. N., Hong, L. H., Carr, P. A. & Kim, P. S. Inhibiting HIV-1 entry: discovery of D-peptide inhibitors that target the gp41 coiled-coil pocket. *Cell* 99, 103-15 (1999).
12. Root, M. J., Kay, M. S. & Kim, P. S. Protein design of an HIV-1 entry inhibitor. *Science* 291, 884-8 (2001).
13. Chan, D. C., Chutkowski, C. T. & Kim, P. S. Evidence that a prominent cavity in the coiled coil of HIV type 1 gp41 is an attractive drug target. *Proc Natl Acad Sci USA* 95, 15613-7 (1998).
14. Eckert, D. M. & Kim, P. S. Design of potent inhibitors of HIV-1 entry from the gp41 N-peptide region. *Proc Natl Acad Sci USA* 98, 11187-92 (2001).
15. Louis, J. M., Nesheiwat, I., Chang, L., Clore, G. M. & Bewley, C. A. Covalent trimers of the internal N-terminal trimeric coiled-coil of gp41 and antibodies directed against them are potent inhibitors of HIV envelope-mediated cell fusion. *J Biol Chem* 278, 20278-85 (2003).
16. Wild, C. T., Shugars, D. C., Greenwell, T. K., McDanal, C. B. & Matthews, T. J. Peptides corresponding to a predictive alpha-helical domain of human immunodeficiency virus 17. Rimsky, L. T., Shugars, D. C. & Matthews, T. J. Determinants of human immunodeficiency virus type 1 resistance to gp41-derived inhibitory peptides. *J Virol* 72, 986-93 (1998).
18. Wei, X. et al. Emergence of resistant human immunodeficiency virus type 1 in patients receiving fusion inhibitor (T-20) monotherapy. *Antimicrob Agents Chemother* 46, 1896-905 (2002).
19. Milton, R. C., Milton, S. C. & Kent, S. B. Total chemical synthesis of a D-enzyme: the enantiomers of HIV-1 protease show reciprocal chiral substrate specificity. *Science* 256, 1445-8 (1992).
20. Sadowski, M. et al. A synthetic peptide blocking the apolipoprotein E/beta-amyloid binding mitigates beta-amyloid toxicity and fibril formation in vitro and reduces beta-amyloid plaques in transgenic mice. *Am J Pathol* 165, 937-48 (2004).
21. Pappenheimer, J. R., Dahl, C. E., Karnovsky, M. L. & Maggio, J. E. Intestinal absorption and excretion of octapeptides composed of D amino acids. *Proc Natl Acad Sci USA* 91, 1942-5 (1994).
22. Pappenheimer, J. R., Karnovsky, M. L. & Maggio, J. E. Absorption and excretion of undegradable peptides: role of lipid solubility and net charge. *J Pharmacol Exp Ther* 280, 292-300 (1997).
23. Schumacher, T. N. et al. Identification of D-peptide ligands through mirror-image phage display. *Science* 271, 1854-7 (1996).
24. Judice, J. K. et al. Inhibition of HIV type 1 infectivity by constrained alpha-helical peptides: implications for the viral fusion mechanism. *Proc Natl Acad Sci USA* 94, 13426-30 (1997).
25. Jin, B. S., Ryu, J. R., Ahn, K. & Yu, Y. G. Design of a peptide inhibitor that blocks the cell fusion mediated by glycoprotein 41 of human immunodeficiency virus type 1. *AIDS Res Hum Retroviruses* 16, 1797-804 (2000).
26. Sia, S. K., Carr, P. A., Cochran, A. G., Malashkevich, V. N. & Kim, P. S. Short constrained peptides that inhibit HIV-1 entry. *Proc Natl Acad Sci USA* 99, 14664-9 (2002).
27. Ernst, J. T. et al. Design of a protein surface antagonist based on alpha-helix mimicry: inhibition of gp41 assembly and viral fusion. *Angew Chem Int Ed Engl* 41, 278-81 (2002).
28. Stephens, O. M. et al. Inhibiting HIV fusion with a beta-peptide foldamer. *J Am Chem Soc* 127, 13126-7 (2005).
29. Debnath, A. K., Radigan, L. & Jiang, S. Structure-based identification of small molecule antiviral compounds targeted to the gp41 core structure of the human immunodeficiency virus type 1. *J Med Chem* 42, 3203-9 (1999).
30. Ferrer, M. et al. Selection of gp41-mediated HIV-1 cell entry inhibitors from biased combinatorial libraries of non-natural binding elements. *Nat Struct Biol* 6, 953-60 (1999).
31. Zhao, Q., Ernst, J. T., Hamilton, A. D., Debnath, A. K. & Jiang, S. XTT formazan widely used to detect cell viability inhibits HIV type 1 infection in vitro by targeting gp41. *AIDS Res Hum Retroviruses* 18, 989-97 (2002).
32. Jiang, S. et al. N-substituted pyrrole derivatives as novel human immunodeficiency virus type 1 entry inhibitors that interfere with the gp41 six-helix bundle formation and block virus fusion. *Antimicrob Agents Chemother* 48, 4349-59 (2004).
33. Frey, G. et al. Small molecules that bind the inner core of gp41 and inhibit HIV envelope-mediated fusion. *Proc Natl Acad Sci USA* 103, 13938-43 (2006).
34. Barbas, C. F. *Phage Display: A Laboratory Manual*, (Cold Springs Harbor Laboratory Press, New York, 2001).
35. Cole, J. L. & Garsky, V. M. Thermodynamics of peptide inhibitor binding to HIV-1 gp41. *Biochemistry* 40, 5633-41 (2001).
36. Harris, J. M. & Chess, R. B. Effect of pegylation on pharmaceuticals. *Nat Rev Drug Discov* 2, 214-21 (2003).
37. Steger, H. K. & Root, M. J. Kinetic dependence to HIV-1 entry inhibition. *J Biol Chem* 281, 25813-21 (2006).
38. Miller, M. D. et al. A human monoclonal antibody neutralizes diverse HIV-1 isolates by binding a critical gp41 epitope. *Proc Natl Acad Sci USA* 102, 14759-64 (2005).
39. Bianchi, E. et al. Covalent stabilization of coiled coils of the HIV gp41 N region yields extremely potent and broad inhibitors of viral infection. *Proc Natl Acad Sci USA* 102, 12903-8 (2005).
40. Platt, E. J., Durnin, J. P. & Kabat, D. Kinetic factors control efficiencies of cell entry, efficacies of entry inhibitors, and mechanisms of adaptation of human immunodeficiency virus. *J Virol* 79, 4347-56 (2005).
41. Choudhry, V. et al. Increased efficacy of HIV-1 neutralization by antibodies at low CCR5 surface concentration. *Biochem Biophys Res Commun* 348, 1107-15 (2006).
42. Chong, P., Sia, C., Tripet, B., James, O. & Klein, M. Comparative immunological properties of enantiomeric peptides *Letters in Peptide Science* 3, 99-106 (1996).
43. Hamburger, A. E., Kim, S., Welch, B. D. & Kay, M. S. Steric accessibility of the HIV-1 gp41 N-trimer region. *J Biol Chem* 280, 12567-72 (2005).
44. Otwinowski, Z. & Minor, W. Processing of X-ray diffraction data collected in oscillation mode. *Methods in Enzymology* 276, 307-326 (1997).
45. McCoy, A. J., Grosse-Kunstleve, R. W., Storoni, L. C. & Read, R. J. Likelihood-enhanced fast translation functions. *Acta Crystallogr D Biol Crystallogr* 61, 458-64 (2005).
46. CCP4 (Collaborative Computational Project, N. The CCP4 suite: programs for protein crystallography. *Acta Crystallogr D Biol Crystallogr* 50, 760-3 (1994).
47. Brunger, A. T. et al. Crystallography & NMR system: A new software suite for macromolecular structure determination. *Acta Crystallogr D Biol Crystallogr* 54, 905-21 (1998).
48. Emsley, P. & Cowtan, K. Coot: model-building tools for molecular graphics. *Acta Crystallogr D Biol Crystallogr* 60, 2126-32 (2004).
49. Noren, K. A. & Noren, C. J. Construction of high-complexity combinatorial phage display peptide libraries. *Methods* 23, 169-78 (2001).
50. Sidhu, S. S., Lowman, H. B., Cunningham, B. C. & Wells, J. A. Phage display for selection of novel binding peptides. *Methods Enzymol* 328, 333-63 (2000).

What is claimed is:

1. An isolated composition comprising at least one peptide that interacts with the N-trimer pocket of a viral transmembrane protein wherein the at least one peptide comprises the amino acid sequence of SEQ ID NO: 36.

2. The composition of claim 1, wherein the at least one peptide is linked to at least one other peptide.

3. The composition of claim 2, wherein a crosslinker is used to multimerize the peptides.

4. The composition of claim 3, wherein the crosslinker is PEG.

5. The composition of claim 2, wherein the peptides are crosslinked into branched structures.

6. The composition of claim 2, wherein the N-termini of the peptides are crosslinked.

7. The composition of claim 2, wherein the C-termini of the peptides are crosslinked.

8. The composition of claim 2, wherein the N-terminus of one peptide and the C-terminus of the other peptide are crosslinked.

9. The composition of claim 1, wherein the viral transmembrane protein is HIV gp41.

10. The composition of claim 1, wherein the at least one peptide is selected from any one of SEQ ID NOS: 3, 4, 5, 6, 7, 8, 9, 12, 13, 23, 24, 25, 26, 27, 28, 29, or a fragment thereof.

11. The composition of claim 1, wherein the composition inhibits viral entry into a cell.

12. The composition of claim 1, wherein at least one peptide is a D-peptide.

13. The composition of claim 1, wherein the composition further comprises a pharmaceutically acceptable carrier.

* * * * *

SEQUENCE LISTING

<160> NUMBER OF SEQ ID NOS: 38

<210> SEQ ID NO 1
<211> LENGTH: 18

-continued

```
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Lys Lys Gly Ala Cys Glu Leu Leu Gly Trp Glu Trp Ala Trp Leu Cys
 1               5                  10                  15

Ala Ala

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Lys Lys Gly Ala Cys Glu Ser Pro Glu Trp Arg Trp Leu Cys Ala Ala
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Lys Lys Gly Ala Cys Asp Tyr Pro Glu Trp Arg Trp Leu Cys Ala Ala
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Lys Gly Ala Cys Asp Tyr Pro Glu Trp Arg Trp Leu Cys Ala Ala Ala
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Lys Gly Ala Cys Asp Tyr Pro Glu Trp Arg Trp Leu Cys Ala Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6
```

```
Lys Gly Ala Cys Asp Tyr Pro Glu Trp Gln Trp Leu Cys Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Lys Gly Ala Cys Asp Tyr Lys Glu Trp Gln Trp Leu Cys Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Lys Gly Ala Cys Asp Tyr Pro Glu Trp Gln Trp Leu Cys Ala Ala
1               5                   10                  15

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Lys Gly Ala Cys Asp Tyr Pro Glu Trp Gln Trp Leu Cys Ala Ala Lys
1               5                   10                  15

Gly Ala Cys Asp Tyr Pro Glu Trp Gln Trp Leu Cys Ala Ala
            20                  25                  30

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Lys Lys Gly Ala Cys Pro Arg Glu Trp His Trp Leu Cys Ala Ala
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Gly Ala Cys Pro Arg Glu Trp His Trp Leu Cys Ala Ala
1               5                   10

<210> SEQ ID NO 12
```

```
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12

Lys Lys Gly Ala Cys Asp Tyr Trp Glu Trp Arg Trp Leu Cys Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Asp Gly Ala Cys Asp Tyr Pro Glu Trp Arg Trp Leu Cys Ala Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14

Lys Lys Gly Ala Cys Asp Asp Pro Asp Trp Gln Trp Leu Cys Ala Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 15

Lys Lys Gly Ala Cys Glu Asp Pro Asp Trp Gln Trp Leu Cys Ala Ala
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 16

Lys Lys Gly Ala Cys Glu Asp Pro Glu Trp Gln Trp Leu Cys Ala Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 17
```

```
Lys Lys Gly Ala Cys Asn Asp Pro Glu Trp Gln Trp Leu Cys Ala Ala
1               5                   10                  15
```

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 18

```
Asp Gly Ala Cys Glu Ser Pro Glu Trp Gln Trp Leu Cys Ala Ala Gly
1               5                   10                  15

Ala Ala
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

```
Ala Cys Pro Pro Glu Trp His Trp Leu Cys Gly Gly Gly Ser Ala
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

```
Ala Cys Pro Val Glu Trp Arg Trp Leu Cys Gly Gly Gly Ser Ala
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

```
Ala Cys Pro Ile Glu Trp Arg Trp Leu Cys Gly Gly Gly Ser Ala
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 22

```
Ala Cys Pro Arg Glu Trp His Trp Leu Cys Gly Gly Gly Ser Ala
1               5                   10                  15
```

<210> SEQ ID NO 23
<211> LENGTH: 16
<212> TYPE: PRT

```
<213> ORGANISM: Artificial Sequence
<220> FEATURE:
<223> OTHER INFORMATION: Description of Artificial Sequence; note =
      synthetic construct

<400> SEQUENCE: 23

Gly Ala Cys Asp Tyr Pro Glu Trp Gln Trp Leu Cys Ala Ala Gly Lys
 1               5                  10                  15

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 24

Gly Ala Cys Asp Tyr Pro Glu Trp Gln Trp Leu Cys Ala Ala Gly Lys
 1               5                  10                  15

Lys

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 25

Lys Gly Ala Cys Asp Tyr Pro Glu Trp Gln Trp Leu Cys Ala Ala Gly
 1               5                  10                  15

Lys

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 26

His Pro Cys Asp Tyr Pro Glu Trp Gln Trp Leu Cys Glu Leu Gly Lys
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 27

His Pro Cys Asp Tyr Pro Glu Trp Gln Trp Leu Cys Lys Leu Gly Lys
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct
```

```
<400> SEQUENCE: 28

His Pro Cys Asp Tyr Pro Glu Trp Gln Trp Leu Cys Arg Leu Gly Lys
  1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29

His Ala Cys Asp Tyr Pro Glu Trp Gln Trp Leu Cys Glu Leu Gly Lys
  1               5                  10                  15

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 3
<223> OTHER INFORMATION: Xaa = Any Amino Acid

<400> SEQUENCE: 30

Glu Trp Xaa Trp Leu
  1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2
<223> OTHER INFORMATION: Xaa = Any Amino Acid

<400> SEQUENCE: 31

Trp Xaa Trp Leu
  1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 32

Lys Lys Gly Ala Cys
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
```

<222> LOCATION: 2, 5
<223> OTHER INFORMATION: Xaa = Any Amino Acid

<400> SEQUENCE: 33

Cys Xaa Glu Trp Xaa Trp Leu Cys
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2, 5
<223> OTHER INFORMATION: Xaa = Any Amino Acid

<400> SEQUENCE: 34

Cys Xaa Glu Trp Xaa Trp Leu Cys
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2, 4
<223> OTHER INFORMATION: Xaa = Any Amino Acid

<400> SEQUENCE: 35

Cys Xaa Trp Xaa Trp Leu Cys
 1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 4, 7
<223> OTHER INFORMATION: Xaa = Any Amino Acid

<400> SEQUENCE: 36

Cys Asp Tyr Xaa Glu Trp Xaa Trp Leu Cys
 1               5                  10

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 34, 35, 40, 41, 43, 44, 46, 47, 49, 50
<223> OTHER INFORMATION: n = A,T,C or G

<400> SEQUENCE: 37
catgtttcgg ccgcgcccgc cgcgcacagc camnnccamn nmnnmnnmnn acacgcgcca    60

```
tcagaatgag                                                                70

<210> SEQ ID NO 38
<211> LENGTH: 54
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 38
aaaaaaaaaa aaaaaaaaaa ggtacctttc tattctcatt ctgatggcgc gtgt            54
```